US012703728B2

(12) United States Patent
Yang et al.

(10) Patent No.: US 12,703,728 B2
(45) Date of Patent: Aug. 11, 2026

(54) INTERLEUKIN 29 MUTANT PROTEIN

(71) Applicant: SCIWIND BIOSCIENCES CO., LTD., Hangzhou Zhejiang (CN)

(72) Inventors: Liu Yang, Beijing (CN); Yan Li, Beijing (CN); Jing Feng, Beijing (CN); Wanjun Guo, Beijing (CN); Hai Pan, Beijing (CN)

(73) Assignee: Sciwind Biosciences Co., Ltd., Hangzhou Zhejiang (CN)

( * ) Notice: Subject to any disclaimer, the term of this patent is extended or adjusted under 35 U.S.C. 154(b) by 796 days.

(21) Appl. No.: 17/999,884

(22) PCT Filed: Feb. 8, 2021

(86) PCT No.: PCT/CN2021/075907

§ 371 (c)(1),
(2) Date: Nov. 25, 2022

(87) PCT Pub. No.: WO2021/238302

PCT Pub. Date: Dec. 2, 2021

(65) Prior Publication Data

US 2023/0265144 A1 Aug. 24, 2023

(30) Foreign Application Priority Data

May 27, 2020 (WO) ................ PCT/CN2020/092613

(51) Int. Cl.

| | |
|---|---|
| ***C07K 14/54*** | (2006.01) |
| ***A61K 9/00*** | (2006.01) |
| ***A61K 38/20*** | (2006.01) |
| ***A61K 47/10*** | (2017.01) |
| ***A61P 31/12*** | (2006.01) |
| ***A61P 35/00*** | (2006.01) |

(52) U.S. Cl.

CPC ............ *C07K 14/54* (2013.01); *A61K 9/0078* (2013.01); *A61K 38/20* (2013.01); *A61K 47/10* (2013.01); *A61P 31/12* (2018.01); *C07K 2319/00* (2013.01)

(58) Field of Classification Search

None

See application file for complete search history.

(56) References Cited

U.S. PATENT DOCUMENTS

| | | | |
|---|---|---|---|
| 10,246,501 B2 | 4/2019 | Liu et al. | |
| 11,242,371 B2 | 2/2022 | Liu et al. | |
| 2007/0053933 A1 | 3/2007 | Sheppard | |
| 2011/0305663 A1* | 12/2011 | Gosselin ................ | A61K 47/62 514/6.9 |
| 2017/0022259 A1 | 1/2017 | Liu et al. | |
| 2019/0382461 A1 | 12/2019 | Liu et al. | |

FOREIGN PATENT DOCUMENTS

| | | |
|---|---|---|
| CN | 101031316 A | 9/2007 |
| CN | 101829318 A | 9/2010 |
| CN | 103224951 A | 7/2013 |
| CN | 103224952 A | 7/2013 |
| CN | 103923209 A | 7/2014 |
| CN | 104402988 A | 3/2015 |
| CN | 104968673 A | 10/2015 |
| CN | 105085657 A | 11/2015 |
| CN | 105085658 A | 11/2015 |
| CN | 107698682 A | 2/2018 |
| CN | 109293782 A | 2/2019 |
| JP | 2013-531477 A | 8/2013 |
| JP | 2017-503505 A | 2/2017 |
| WO | WO 2006/012644 A2 | 2/2006 |
| WO | WO 2011/140086 A2 | 11/2011 |
| WO | WO 2015/103749 A1 | 7/2015 |

OTHER PUBLICATIONS

Balducci L (2016) Seminars Oncology Nursing, 32: 314-324.*
Kelm et al. (2016) The role of IL-29 in immunity and cancer. Critical Reviews in Oncology/Hematology, 106: 91-98.*
Tang et al. (2025) IFN-λ: Unleashing Its Potential in Disease Therapies from Acute Inflammation Regulation to Cancer Immunotherapy. Immunology, 176: 197-214.*
Brain et al., "Pulmonary distribution of particles given by intratracheal instillation or by aerosol inhalation," *Environ Res* 11(1): 13-33 (1976).
Japan Patent Office, Notice of Reasons for Refusal in Japanese Patent Application No. 2022-572748 (Sep. 3, 2024).
Dumoutier et al. "Role of the Interleukin (IL)-28 Receptor Tyrosine Residues for Antiviral and Antiproliferative Activity of IL-29/Interferon-λl: Similarities With Type I Interferon Signaling," *Journal of Biological Chemistry* 279(31): 32269-32274 (2004)pp.
Kotenko et al., IFN-λs mediate antiviral protection through a distinct class II cytokine receptor complex, *Nature Immunology* 4(1): 69-77 (2003).
La Fleur et al., "Interferon-κ, a Novel Type I Interferon Expressed in Human Keratinocytes," *J. Biol. Chem.* 276(43): 39765-39771 (2001).
Li et al., "Site-directed Mutation on Lys43 of hIL-29 and Antineoplastic Analysis of the Variant," *Chinese Journal of Pharmaceuticals* 47(3): 282-287 (2016).
China National Intellectual Property Administration, International Search Report in International Application No. PCT/2021/075907 (Apr. 29, 2021).
China National Intellectual Property Administration, Written Opinion in International Application No. PCT/2021/075907 (Apr. 29, 2021).
International Bureau of Wipo, International Preliminary Report on Patentability in International Application No. PCT/2021/075907 (Nov. 17, 2022).

* cited by examiner

*Primary Examiner* — Ilia I Ouspenski

(74) *Attorney, Agent, or Firm* — Leydig, Voit & Mayer, Ltd.

(57) ABSTRACT

Provided are an interleukin 29 (IL29) mutant protein, and a fusion protein, a conjugate, a pharmaceutical composition, a product and a kit which comprises the mutant protein. The provided IL29 mutant protein has good activity and stability, and can effectively prevent and/or treat viral infectious diseases, tumors and other diseases needing to regulate the body immune function.

6 Claims, 21 Drawing Sheets

Specification includes a Sequence Listing.

INTERLEUKIN 29 MUTANT PROTEIN

CROSS-REFERENCE TO RELATED APPLICATIONS

This patent application is the U.S. national phase of International Application No. PCT/CN2021/075907, filed on Feb. 8, 2021, which claims the benefit of International Application No. PCT/CN2020/092613, filed May 27, 2020, the disclosures of which are incorporated herein by reference in their entireties for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 22,986 byte ASCII (Text) file named "766279_SQL-Rep1.txt", dated May 10, 2023.

TECHNICAL FIELD

The present application relates to the field of prevention and/or treatment by using a peptide, particularly the present application relates to an interleukin 29 (IL29) mutant protein, and a fusion protein, conjugate and composition comprising the mutant protein, which can be used for improving the body's resistance to viruses and modulating the body's immune function.

BACKGROUND ART

Interferons are an important family of cytokines with broad-spectrum antiviral and immunomodulatory effects. To date, seven forms of interferons (α, β, ω, δ, τ, γ, and λ) have been identified, which are divided into three major groups: type I, type II and type III. The so-called "type I" interferons include interferon α, interferon β, interferon ω, interferon δ, and interferon τ. Currently, interferon γ is the only type II interferon. Type III interferons are a recently discovered family of cytokines that includes interferons 21, 22 and 23, also known as IL-28A, IL-28B and IL-29.

IL-28A, IL-28B and IL-29 share sequence homology with type I interferons, and have gene sequence homology with IL-10. Functionally, IL-28 and IL-29 are similar to type I interferons in that both induce antiviral effects in cells; and unlike type I interferons, they do not show anti-proliferative activity against certain B-cell lines.

The wild-type IL-29 (interferon 21, abbreviated as IFN-λ1) gene encodes a 200 amino acid protein, as represented by SEQ ID NO: 3, particularly amino acids 1-19 in this sequence are the signal peptide sequence, and the mature amino acid sequence of this protein has 181 amino acids, as represented by SEQ ID NO: 2. The IL-29 molecule is composed of six protein helices A-F, wherein helices A, C, D and F form a classical up-up-down-down quadruple helix bundle. IL-29 initiates downstream signaling pathways by interacting with its receptor complex. The receptor complex of which is composed of IFN-λR1 and IL-10R2. Notably, IFN-λR1 is specific to the IFN-λ signaling pathway. IFN-λ1 binds specifically to IFN-λR1 to form the IFN-λ1/IFN-λR1 complex, wherein the amino acid residues of the active center for the binding of IFN-λ1 and IFN-λR1 are Pro25, Leu28, lys32, Arg35, Asp36 Glu39, Trp47, Phe152, Phe155, Arg156, and Arg160.

Whether it is type I interferon, type II interferon or type III interferon, as a protein drug, it is greatly limited in clinical therapeutic application due to poor stability, low activity and short half-life in vivo. Therefore, it is desirable to obtain recombinant interferon protein drugs with higher stability and specific activity by genetic engineering technology. In particular, the prevention and/or treatment of respiratory diseases by aerosol inhalation therapy requires nebulizing the drug solution into tiny particles by nebulizer, thereby being inhaled into the respiratory tract and lungs to deposit the drug in the respiratory tract and lungs. This situation requires higher stability and activity of the drug, and therefore it is in urgent need of a recombinant IL29 protein with higher stability and better activity. Genetic engineering techniques have been used to alter one or more amino acids in a wild protein sequence to obtain a recombinant protein with relatively higher stability and specific activity, which can solve the instability problems caused by protein drugs to some extent. However, the mutation of one or several amino acids may affect the folding and spatial structure of a protein, thus affecting the activity of the protein. Therefore, whether an IL29 mutant protein with higher stability and better activity can be obtained is a difficult technical problem.

SUMMARY OF THE APPLICATION

In summary, to solve the problems of the prior art, the present application provides an IL29 mutant protein with higher stability, better activity, less adverse effects, and it is useful in aerosol inhalation therapy.

In one aspect, the present application provides an interleukin 29 (IL29) mutant protein comprising a substitution mutation at amino acid position 161 or 162 of the amino acid sequence represented by SEQ ID NO: 1, wherein the aspartic acid (D) at position 161 or the glycine (G) at position 162 is substituted with another natural amino acid.

In some embodiments, the interleukin 29 (IL29) mutant protein of the present application comprises a substitution of the aspartic acid (D) at position 161 of the amino acid sequence represented by SEQ ID NO: 1 with a glutamic acid, a threonine or serine, or a substitution of the glycine (G) at position 162 with an aliphatic amino acid.

In some embodiments, the interleukin 29 (IL29) mutant protein of the present application further comprises a substitution mutation from cysteine (C) to serine(S) at amino acid position 165 of the amino acid sequence represented by SEQ ID NO: 1.

In the present application, the amino acid sequence of the full-length wild-type IL29 protein comprising the signal peptide is represented by SEQ ID NO: 3, consisting of 200 amino acids, wherein the amino acids 1-19 are the signal peptide, and the amino acids 20-200 (181aa) constitute the mature protein of IL29 (the amino acid sequence represented by SEQ ID NO: 2).

The interleukin 29 (IL29) mutant protein of this application was designed by starting at position 26 from the N-terminal of the wild-type protein represented by SEQ ID NO: 3. The interleukin 29 (IL29) mutant protein of the present application comprises an amino acid substitution mutation at position 161 or 162 of the amino acid sequence represented by SEQ ID NO: 1.

In some embodiments of the present application, provided herein is an interleukin 29 (IL29) mutant protein comprising a substitution mutation at amino acid position 161 or 162 of the amino acid sequence represented by SEQ ID NO: 1, wherein the aspartic acid (D) at position 161 or the glycine (G) at position 162 is substituted with another natural amino acid, such as being substituted with an amino acid selected from the group consisting of: glycine, alanine, valine, leucine, isoleucine, methionine, proline, tryptophan, serine, tyrosine, cysteine, phenylalanine, asparagine, glutamine, threonine, aspartic acid, glutamic acid, lysine, arginine or histidine.

The correspondence between positions 161 and 162 of SEQ ID NO: 1 and the corresponding positions of SEQ ID NO: 2 (wild-type interleukin 29 mature protein) and SEQ ID NO: 3 (wild-type interleukin 29 full-length protein comprising a signal peptide) can be understood by those of skill in the art, therefore amino acid mutations at the corresponding positions based on SEQ ID NO: 2 or SEQ ID NO: 3 (or amino acid sequences of different lengths derived from SEQ ID NO: 2 or SEQ ID NO: 3) are also covered by the protection scope of this application. The protection scope of this application also covers interleukin 29 mutant proteins derived from SEQ ID NO. 2 or SEQ ID NO: 3, but having amino acid sequences of different lengths, which comprises substitution mutations at the corresponding positions of positions 161 and 162 described above.

In some embodiments of the above interleukin 29 (IL29) mutant protein, the interleukin 29 (IL29) mutant protein comprises a substitution mutation at amino acid position 161 or 162 of the amino acid sequence represented by SEQ ID NO: 1, wherein the aspartic acid (D) at position 161 or the glycine (G) at position 162 is substituted with another natural amino acid, and further comprises the starting methionine (M). This is because when IL29 is expressed in a prokaryotic cell (e.g., *E. coli*), an N-terminal or amino-terminal methionine presents in the expressed IL29 protein.

In some embodiments of the present application, the IL-29 mutant protein of the present application comprises a substitution mutation at the amino acid position 161 or 162 of the amino acid sequence represented by SEQ ID NO: 1, i.e., a mutation at position 161 or 162 counting from the N-terminal or amino-terminal of the protein represented by SEQ ID NO: 1, for example the aspartic acid at position 161 (D) or the glycine (G) at position 162 is substituted with another natural amino acid. In some embodiments, the IL-29 mutant protein of the present application is a mutant protein expressed in a prokaryotic cell (e.g., *E. coli*), which comprises a substitution mutation at position 162 or 163 (counting from M, because of the addition of the N-terminal M), for example, the aspartic acid (D) at position 162 or the glycine (G) at position 163 is substituted with another natural amino acid. In a particular embodiment, the IL-29 mutant protein of the present application is represented by SEQ ID NOs: 4-9.

In some embodiments of the above interleukin 29 (IL29) mutant protein, the interleukin 29 (IL29) mutant protein comprises a substitution mutation at amino acid position 161 or 162 of the amino acid sequence represented by SEQ ID NO: 1, for example, wherein the aspartic acid (D) at position 161 is substituted with glutamic acid, threonine or serine; or wherein the glycine (G) at position 162 is substituted with an aliphatic amino acid. In some embodiments, the IL-29 mutant protein of this application is a mutant protein expressed in a prokaryotic cell (e.g., *E. coli*), which comprises a substitution mutation at position 162 or 163 (counting from M, because of the addition of the N-terminal M), for example, wherein the aspartate (D) at position 162 is substituted with a glutamate, a threonine, or a serine; or wherein the glycine (G) at position 163 is substituted with an aliphatic amino acid (G).

In some embodiments of the above interleukin 29 (IL29) mutant protein, the interleukin 29 (IL29) mutant protein comprises or consists of the amino acid sequence: SEQ ID NO: 4, SEQ ID NO: 6, or SEQ ID NO: 8.

In some embodiments of the above interleukin 29 (IL29) mutant protein, the interleukin 29 (IL29) mutant protein further comprises a substitution mutation from cysteine (C) to serine(S) at position 165 of the amino acid sequence represented by SEQ ID NO: 1. As described above, when the IL29 mutant protein is expressed in a prokaryotic cell (e.g., *E. coli*), the substitution mutation from cysteine (C) to serine(S) at position 165 presents at position 166.

In some embodiments of the above interleukin 29 (IL29) mutant protein, the interleukin 29 (IL29) mutant protein comprises or consists of the amino acid sequence of: SEQ ID NO: 5, SEQ ID NO: 7 or SEQ ID NO: 9.

In some embodiments of the present application, the present application provides an interleukin 29 (IL29) mutant protein (IL29 DE) represented by SEQ ID NO: 4 below:

```
                                            (SEQ ID NO: 4)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVAEGNLCLRTSTHPEST.
```

In some embodiments, the present application provides a 29 (IL29) mutant protein (IL29 DE+CS) represented by SEQ ID NO: 5 below:

```
                                            (SEQ ID NO: 5)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVAEGNLSLRTSTHPEST.
```

In some embodiments, the present application provides a 29 (IL29) mutant protein (IL29 DS) represented by SEQ ID NO: 6 below:

```
                                            (SEQ ID NO: 6)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVASGNLCLRTSTHPEST.
```

In some embodiments, the present application provides a 29 (IL29) mutant protein (IL29 DS+CS) represented by SEQ ID NO: 7 below:

```
                                            (SEQ ID NO: 7)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVASGNLSLRTSTHPEST.
```

In some embodiments, the present application provides a 29 (IL29) mutant protein (IL29 GA) represented by SEQ ID NO: 8 below:

(SEQ ID NO: 8)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVADANLCLRTSTHPEST.

In some embodiments, the present application provides a 29 (IL29) mutant protein (IL29 GA+CS) represented by SEQ ID NO: 9:

(SEQ ID NO: 9)
MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVADANLSLRTSTHPEST.

In some embodiments of the above interleukin 29 (IL29) mutant protein, the interleukin 29 (IL29) mutant protein further comprises a short sequence (e.g., a short sequence of 6 histidines) for facilitating protein purification, or a short amino acid sequence for extending the half-life.

In some embodiments, the present application relates to a fusion protein of the interleukin 29 (IL29) mutant protein, wherein the interleukin 29 (IL29) mutant protein is fused to another polypeptide or protein at the N-terminal or C-terminal. For example, it can be fused with human albumin, transferrin, the Fc portion of the human IgG molecule, etc. to form a fusion protein to increase the in vivo half-life of the protein. The interleukin 29 (IL29) mutant protein may also be fused with another protein targeting a different target to collaboratively play a role in prevention and/or treatment, and to improve the prevention and/or treatment effect of the medicament. For example, the mutant protein of the present application can be fused with DAS181 to enhance the activity in preventing and/or treating virus. DAS181 uses a unique host-directed approach to block respiratory virus transmission by turning off sialic acid receptors in the human respiratory tract. These receptors bind to most major respiratory viruses, resulting in infection in patients. DAS181 has shown antiviral activity against four major respiratory viruses, including influenza virus (IFV), parainfluenza virus (PIV), metapneumovirus (MPV), and human enterovirus-68 (EV-68).

In some embodiments, the present application relates to a conjugate of the interleukin 29 (IL29) mutant protein, wherein the protein is conjugated to a polyalkoxide. The polyalkoxide is for example polyethylene glycol (PEG) (e.g. straight or branched polyethylene glycol), particularly monomethoxy polyethylene glycol propionaldehyde (mPEG propionaldehyde) (e.g. 20 kD, 30 kD or 40 kD mPEG propionaldehyde). The process of modifying the interleukin 29 mutant protein with PEG to form a conjugate is referred to as PEGylation. PEGylation of the mutant protein in this application can be performed by any of the PEGylation methods known in the prior art, for example, by acylation reaction or alkylation reaction. The therapeutic half-life of a protein can be artificially increased by conjugating one or more PEGs to the protein to increase the overall size, thereby avoiding rapid degradation in vivo.

In some embodiments, the present application relates to a polynucleotide encoding any of the above proteins or fusion proteins.

In some embodiments, the present application relates to a vector comprising a polynucleotide as described above. In brief, a polynucleotide encoding the interleukin 29 (IL29) mutant protein is inserted into a suitable expression vector, such that the polynucleotide is operably linked to a polyclonal site for expression of the corresponding protein.

The vector can be a pET series vector, such as pET-3a, pET-9a, pET-11a, pET-14b, pET-15b, pET-16b, 17b, 19b, 20b, 21a, 22b, 23a(+), 24a, 25b(+), 26b(+), 27b(+), 28a(+), 29a(+) 30a(+), 31b(+), 32a(+), 39b(+), 40b(+), 41a(+), 42a (+), 43.1a(+), 44b, 45b, 47b, 48b, 49b(+), 50b(+), 51b(+), 52b(+); a pMal series vector, such as pMal-c2X, pMal-c5X; a pGEX series vector, such as pGEX-6p-1, pGEX-6P-2; a pRSET series vector, such as pRSET A, B and C; a pTricHis series vector, such as pTrcHis A, B and C. Preferably, the vector is pET-30a(+).

In some embodiments, the present application relates to a host cell comprising the polynucleotide or the vector as described above. The host cell is used to express the IL29 mutant protein of the present application. A host cell is a recipient cell that receives an exogenous gene by, for example, transformation or transduction. Common host cells are prokaryotic recipient cells and eukaryotic recipient cells. In this present application, preferably a prokaryotic recipient cell is selected as the host cell. Particularly, the host cell is an *E. coli* competent cell BL21 (DE3), Tuner (DE3), Origami (DE3), Rosetta (DE3), JM109 (DE3), BL21 star (DE3), Rosetta-gami (DE3), Rosetta-gami B (DE3), BL21 (DE3) pLysS or BL21 star (DE3) pLysS. Preferably, the host cell is an *E. coli* competent cell BL21 (DE3).

In some embodiments, the present application relates to a pharmaceutical composition comprising the above IL29 mutant protein, a fusion protein thereof or a conjugate thereof, and a pharmaceutically acceptable carrier.

The pharmaceutical composition may be in the form of an injection, a tablet, a capsule, an inhalant, a suppository, etc. Preferably, the pharmaceutical composition is an inhalant, for example, a dry powder inhalant or a liquid inhalant, such as a nebulized inhalant, an aerosol, a soft mist, and a spray, etc., which is administered by an inhalation device, such as a nebulizer, a metered dose inhaler, and a dry powder inhaler.

In some embodiments, the pharmaceutical composition of the present application comprising the IL29 mutant protein, the fusion protein or the conjugate thereof further comprises a carrier suitable for pulmonary administration for the prevention and/or treatment of various respiratory viral infections.

In some embodiments, the pharmaceutical composition of the present application comprising the IL29 mutant protein, the fusion protein or the conjugate thereof further comprises a carrier suitable for pulmonary administration for the prevention and/or treatment of disease caused by novel coronavirus (e.g., SARS-COV-2) infection.

In some embodiments, the present application relates to a method for preparing the interleukin 29 (IL29) mutant protein, the method comprises: introducing a nucleic acid (polynucleotide) encoding the interleukin 29 (IL29) mutant protein into a host cell, such that the host cell expresses the interleukin 29 (IL29) mutant protein, for example, inserting the nucleic acid into an expression vector; transferring the vector into a host cell (e.g., *E. coli*) to obtain a corresponding host cell (engineered bacterium) expressing the mutant protein; culturing (e.g., fermenting) the host cell (engineered bacterium), and inducing the host cell (engineered bacterium) to express the mutant protein, finally harvesting the mutant protein.

In some embodiments, the above method further comprises purifying the harvested mutant protein and/or renaturing the mutant protein.

BRIEF DESCRIPTION OF THE DRAWINGS

in FIG. 2, lanes 1~4 are in order as follows: IL29CS, IL29DE+CS, IL29DS+CS, and IL29GA+CS).

DETAIL DESCRIPTION OF THE APPLICATION

Figure 1:
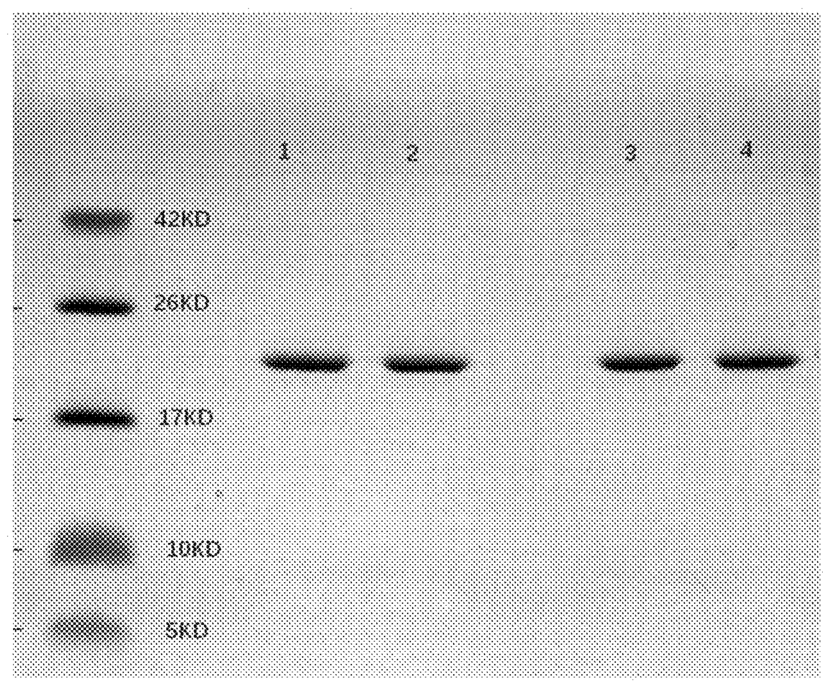
FIGS. 1-2 show the SDS-PAGE electrophoresis of the IL29 mutant of Example 2 (from left to right, in FIG. 1, lanes 1~4 are in order as follows: IL29 control, IL29DE, IL29DS, and IL29GA.

The present application provides an interleukin 29 (IL29) mutant protein, a fusion protein or a conjugate comprising the mutant protein, a method for preparing the mutant protein, and use of the mutant protein, the fusion protein, the conjugate or the pharmaceutical composition in the prevention and/or treatment of viral infections, oncological diseases, and respiratory distress syndrome. The inventors screened multiple mutation sites and finally found that, compared with the wild-type IL29, the activity of the IL29 mutant protein provided in this application (the IL29 mutant protein obtained after mutation from D to E at position 161 of the non-active center site of the amino acid sequence represented by SEQ ID NO: 1, or the mutant protein expressed in a prokaryotic cell (e.g., *E. coli*) after mutation from D to E at position 162 of SEQ ID NO: 1) is unexpectedly increased by about three times and is more stable, thereby solving the problems of the existing antiviral protein drugs, including low activity, poor stability and serious adverse effects.

Definition

The term "recombinant expression vector" or "vector" is used to refer to a linear or circular DNA molecule comprising a fragment encoding a polypeptide of interest, wherein the fragment is operably linked to an additional fragment providing for its transcription. These additional fragments include promoter and terminator sequences, and may further include one or more replication start points, one or more selection markers, enhancers, polyadenylation signals, etc. Expression vectors are generally derived from plasmid or viral DNA, or may comprise elements of the both.

A "polynucleotide" is a single- or double-chain polymer of the bases of deoxyribonucleotides or ribonucleotides reading from the 5' to the 3' end. Polynucleotides include RNA and DNA and can be prepared by isolation from natural sources, by in vitro synthesis, or by combining natural and synthetic molecules. The size of a polynucleotide is indicated as base pairs (abbreviated as "bp"), nucleotides ("nt") or kilobases ("kb"). Where the context permits, the latter two terms can describe single- or double-chain polynucleotides. Polynucleotides and nucleic acids may be used interchangeably in the present application.

The term "polypeptide" refers to a polymer of amino acid residues linked by peptide bonds, and may be naturally occurring or synthetically occurring. In this application, polypeptide and protein are used interchangeably.

A "mutant" protein is a protein in which the amino acid sequence of the wild-type protein is altered, for example, a protein obtained by mutating the amino acid sequence of a wild-type protein through genetic engineering methods. In this application, the terms "mutated protein", "mutant protein" or "mutant" have the same meaning, and are used interchangeably.

"Pharmacologically acceptable" or "pharmacologically compatible" means a material that is not biologically or otherwise undesirable, for example a material that can be incorporated into a pharmaceutical composition to administer to a patient without causing significant adverse biological effects or interacting with any other component in the composition in a harmful manner. The pharmaceutically acceptable carrier or excipient preferably meets the required criteria for toxicology or production testing, and/or is included in the guidelines for inactive ingredients prepared by the U.S. Food and Drug Administration.

In some embodiments of the present application, provided is a method for preventing and/or treating a viral infection in a subject, the method comprises providing the subject with a therapeutically effective amount of the interleukin 29 (IL29) mutant protein of the present application.

In some embodiments of the present application, provided is a method for preventing and/or treating a tumor, the method comprises providing the subject with a therapeutically effective amount of the interleukin 29 (IL29) mutant protein of the present application.

In some embodiments of the present application, provided is a method for preventing and/or treating or ameliorating respiratory distress syndrome in a subject, the method comprises providing the subject with an effective amount of interleukin 29 (IL29) mutant protein of the present application.

In some embodiments of the present application, provided is a method for preventing and/or treating a disease caused by novel coronavirus (e.g., SARS-COV-2) infection, the method comprises providing a subject with a therapeutically effective amount of the interleukin 29 (IL29) mutant protein of the present application.

As used herein, the term "treatment" refers to obtaining a desired pharmacological and/or physiological effect. The effect may be the complete or partial prevention of the occurrence or onset of the disease and/or symptoms thereof, or partial or complete alleviation of the disease and/or symptoms thereof, and/or partial or complete cure of the disease and/or symptoms thereof, including: (a) prevention of the occurrence or onset of the disease in a subject, wherein the subject may have the precipitating factor of the disease, but not yet diagnosed as having the disease; (b) inhibition of the disease, i.e., impeding its formation; and (c) alleviation of the disease and/or symptoms thereof, i.e., causing the disease and/or symptoms thereof to subside or disappear.

The term "subject" in this application refers to a mammal, including but not limited to a murine (rat, mouse), a non-human primate, a human, a dog, a cat, or a hoofed animal (e.g., horse, cattle, sheep, pig, goat), etc.

A "therapeutically effective amount" or "effective amount" means an amount sufficient to achieve the prevention and/or treatment of a disease when administered to a mammal or another subject for the treatment of the disease. The "therapeutically effective amount" will vary depending on the drug used, the severity of the disease and/or symptoms thereof, age, weight, etc. of the subject to be treated. The person skilled in the art can easily determine the appropriate therapeutically effective amount and frequency of administration of the protein or composition described in the present application based on various parameters, in particular the age, weight and condition of the subject to be treated, the severity of the disease or condition, and the route of administration. Particularly, the routes of administration include, but are not limited to: enteral, topical, suppository, inhalation, and parenteral administration, such as subcutaneous, intramuscular, or intravenous injection.

Common assays for detecting the activity of interleukin 29 (IL29) protein include cytopathic effect (CPE) assay, reporter gene assay, etc., particularly the cytopathic effect (CPE) assay refers to infection of human retinal pigment epithelial cells ARPE-19 by vesicular stomatitis virus (VSV), then evaluating the degree of cellular protection by IL29 through colorimetric method of crystalline violet staining, and thus evaluating IL29 activity (Kotenko Sergei Gallagher Grant, Baurin Vitaliy V et al. IFN-lambdas mediate antiviral protection through a distinct class II cytokine receptor complex. [J]. Nat. Immunol., 2003, 4: 69-77).

The reporter gene method refers to ligating the promoter of interferon-stimulated response element (ISRE) to alkaline phosphatase cDNA, and transfecting them into HEK293 cells, and evaluating IL29 activity by measuring alkaline phosphatase in supernatant of HEK293 cells after IL29 stimulation (LaFleur D W, Nardelli B, Tsareva T Et al. Interferon-kappa, a novel type I interferon expressed in human keratinocytes. [J]. J. Biol. Chem., 2001, 276:39765-71).

Assays for detecting the stability of interleukin 29 (IL29) protein also include a variety of methods, such as reversed-phase high-performance liquid chromatography for analyzing impurities with differences in hydrophobicity and polarity; ion-exchange high-performance liquid chromatography for separating impurities with large differences in charge; and molecular sieve exclusion chromatography for analyzing dimers, polymers, and monomers. Each of these assays has a different focus, but all can be used to characterize the protein purity to know the stability of the protein.

The application is further illustrated by the following non-limiting examples.

EXAMPLES

Example 1: Preparation of IL29 Mutant Proteins 1.1 Construction of Engineered Bacteria Expressing the Mutant Proteins The gene fragments of IL29 mutant proteins (SEQ ID NOs: 11-17) were obtained by chemical synthesis, the above fragments were inserted into the prokaryotic expression plasmid pET-30a(+) (Novagen) through Node I and Xho I sites and verified by sequencing. The resulting expression plasmids were used for transformation assays. The plasmids comprising the target genes obtained above were transformed into *E. coli* BL21 (DE3) competent cells (Invitrogen). 50 μl of BL21 competent cells were melted on an ice bath, then the plasmids were added to shake gently, placing in the ice bath for 30 min, followed by thermal excitation in a 42° C. water bath for 30 seconds, and then the centrifuge tubes were quickly transferred to the ice bath to stand for 2 min, without shaking the tubes during this procedure. 500 μl of sterile LB medium (without antibiotics) was added to the above centrifuge tube to mix well, incubating at 37° C., 180 rpm for 1 hour to recover the bacteria 200 μl of transformed competent cells was pipetted onto LB agar medium plates containing kanamycin resistance, spreading the cells evenly. The plates were placed at 37° C. until the liquid was absorbed, inverting the plates and incubating overnight at 37° C. On the following day, monoclonal colonies in the transformed plates were picked by using an inoculation loop, and inoculated in 15 ml of sterile LB medium (containing kanamycin) to incubate overnight at 30° C.

1.2 Expression and Purification of IL29 Mutant Proteins

50 μl of the above bacterial suspension was added to 50 ml of LB medium, and 50 μl of kanamycin was added at the same time to mix well, placing in a constant temperature shaker at 30° C. to inoculate overnight. 10 ml of the overnight inoculum bacterial suspension was taken to add into 1000 ml of LB medium, and 1000 μl of kanamycin was added at the same time to shake well, placing in a 37° C. shaker to incubate at 200 rpm until the OD600 of the bacterial suspension was 0.4-0.6, adding IPTG at the final concentration of 0.5 mM for inducing, continuing to incubate for 4 h and then collecting the bacteria. The expressed IL29 mutant proteins account for about 30-50% of the total proteins of the bacteria, mainly presenting in the form of inclusion bodies.

The fermented bacteria were washed three times with TE (10 mmol/L Tris-HCl, 1 mmol/L EDTA, pH 6.5) solution (m:V=1:10), then breaking by homogenization under high pressure of 60 Mpa; after homogenization, the fragmentation rate was examined microscopically. When the fragmentation rate was about 95% (about 2-3 times fragmentation), centrifuging at 8000 rpm for 15 min, and collecting the precipitate of fragmentized bacteria. The precipitate of the fragmentized bacteria was taken to place in a beaker, adding inclusion body washing solution (10 mM Tris-HCl+1 mM EDTA+0.5% Triton-X100, pH 6.5, m:V=1:10) to stir for 30 min on a magnetic mixer, and washing 3-5 times. Inclusion bodies were lysed with inclusion body lysis solution (7 M guanidine hydrochloride+50 mM Tris-HCl+10 mM DTT, pH 6.5, m:V=1:10), stirring at room temperature overnight. Renaturation solution (100 mM Tris-HCl, 0.5 M arginine, 0.5% PEG3350 (m:V), 2 mM GSH: 0.5 mM GSSG, pH 8.5) was slowly added in the lysed protein to a final protein concentration of 0.2 mg/ml, stirring at room temperature overnight.

The renaturation solution comprising the lysed protein was centrifuged at 8000 rpm for 5 min, and the supernatant was collected. An ultrafiltration membrane package with an ultrafiltration membrane pore size of 10 kDa was used for concentration, and the ultrafiltration membrane was equilibrated with 20 mM phosphate buffer (pH 7.0), then 1 L of supernatant was concentrated 10-fold. The concentrated solution was diluted with 5 times volume of water for injection to be used for sample loading, the column was packed with Sepharose FF and equilibrated with 50 mmol/L Tris-HCl (pH 8.5) and 0.1 mol/L NaCl, and the sample was loaded; then 50 mmol/L Tris-HCl (pH 8.5) and 0.15 mol/L NaCl were used for eluting the sample, collecting the elution peak fraction to obtain 600 ml of final sample elution solution; the column was packed with Sepharose FF, and equilibrated with 20 mmol/L phosphate (pH 7.4) and 0.05 mol/L NaCl, then the sample was loaded until the baseline of the detector was smooth. The column was washed with 20 mmol/L phosphate (pH 7.4) and 0.2 mol/L NaCl, and the elution peak fraction was collected.

Seven IL29 mutant proteins (referred to as IL29 mutants) were obtained, corresponding to the protein amino acid sequences SEQ ID NOs: 4-10, named IL29DE, IL29DE+CS, IL29DS, IL29 DS+CS, IL29GA, IL29GA+CS, and IL29CS, respectively.

Similarly, IL29 wild-type protein (referred to as IL29 control) was synthesized with the same method described above, corresponding to the protein amino acid sequence SEQ ID NO: 1 with an additional M amino acid at the N-terminal.

Example 2: Detection of Various Indicators of the Obtained IL29 Mutant 2.1 Detection of Molecular Weight and Purity of the Obtained IL29 Mutant by SDS-PAGE Electrophoresis.

SDS-PAGE electrophoresis loading buffer was used, under the condition of adding mercaptoethanol, Marker and 10 μg of the above obtained proteins were loaded separately, and electrophoresis was performed at a constant voltage of 200 V for 45 min. The proteins were stained with Komas Brilliant Blue G-25, and the protein molecular weight and purity were detected; and the results are shown in FIGS. 1-2.

Figure 2:
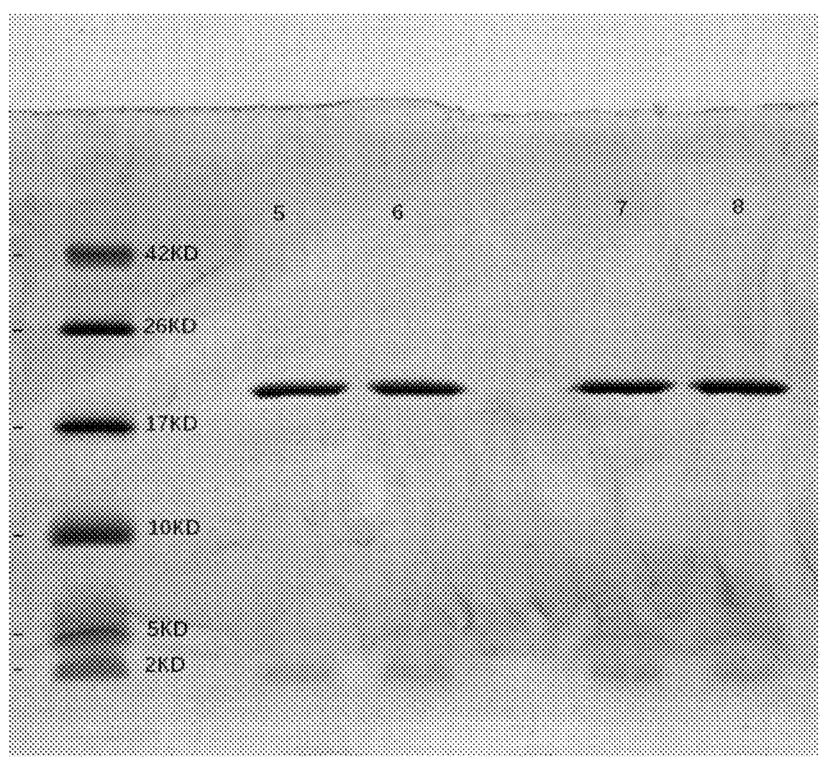
Figure 3:
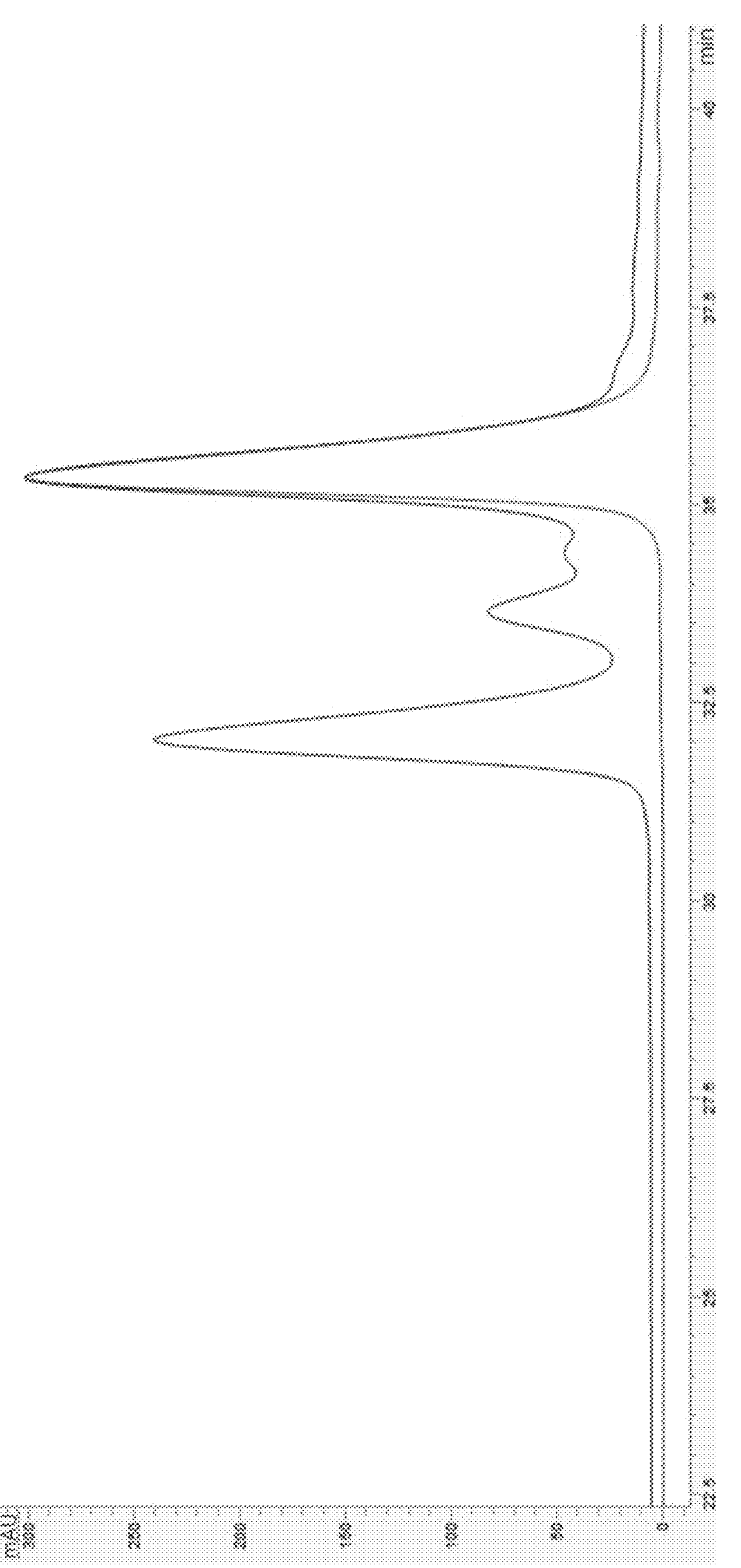
FIGS. 3-10 show the reversed-phase HPLC purity profiles of stability testing of IL29 control, IL29DE, IL29DS, IL29GA, IL29CS, IL29DE+CS, IL29DS+CS, and IL29GA+CS respectively (wherein the curve having a high main peak content represents the 0-point assay curve, and the curve having a low main peak content represents the day 14 curve).
Figure 4:
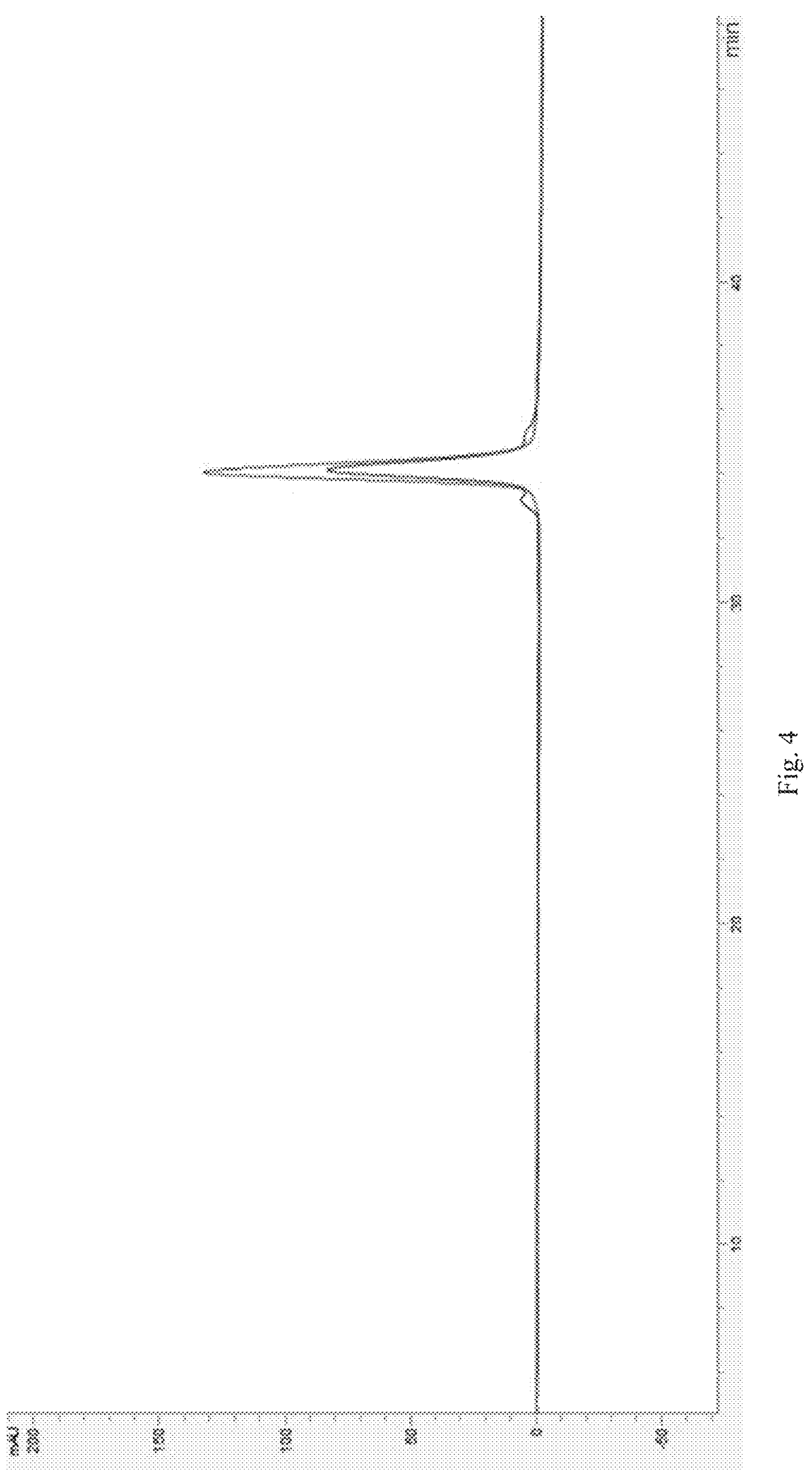
Figure 5:
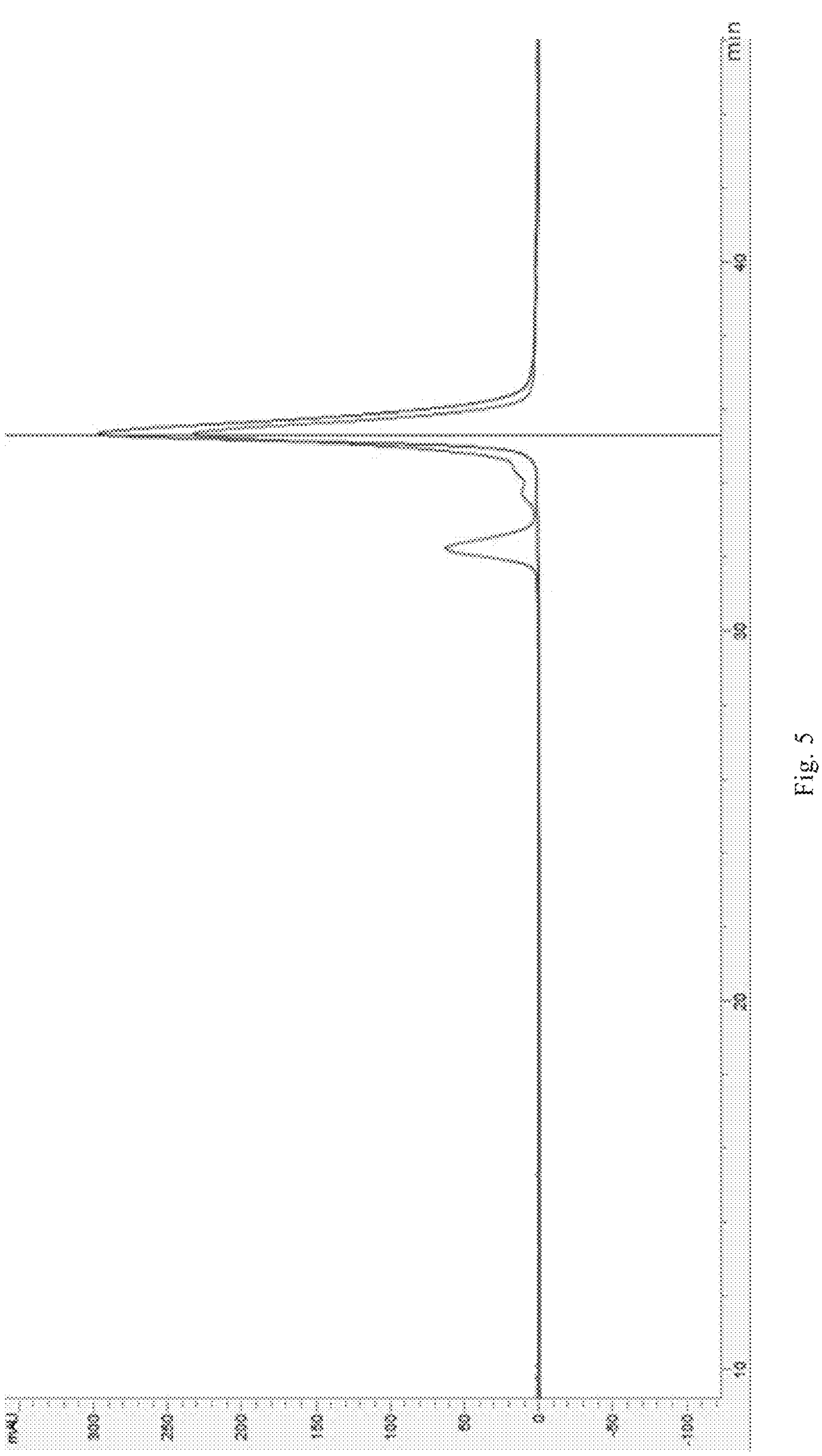
Figure 6:
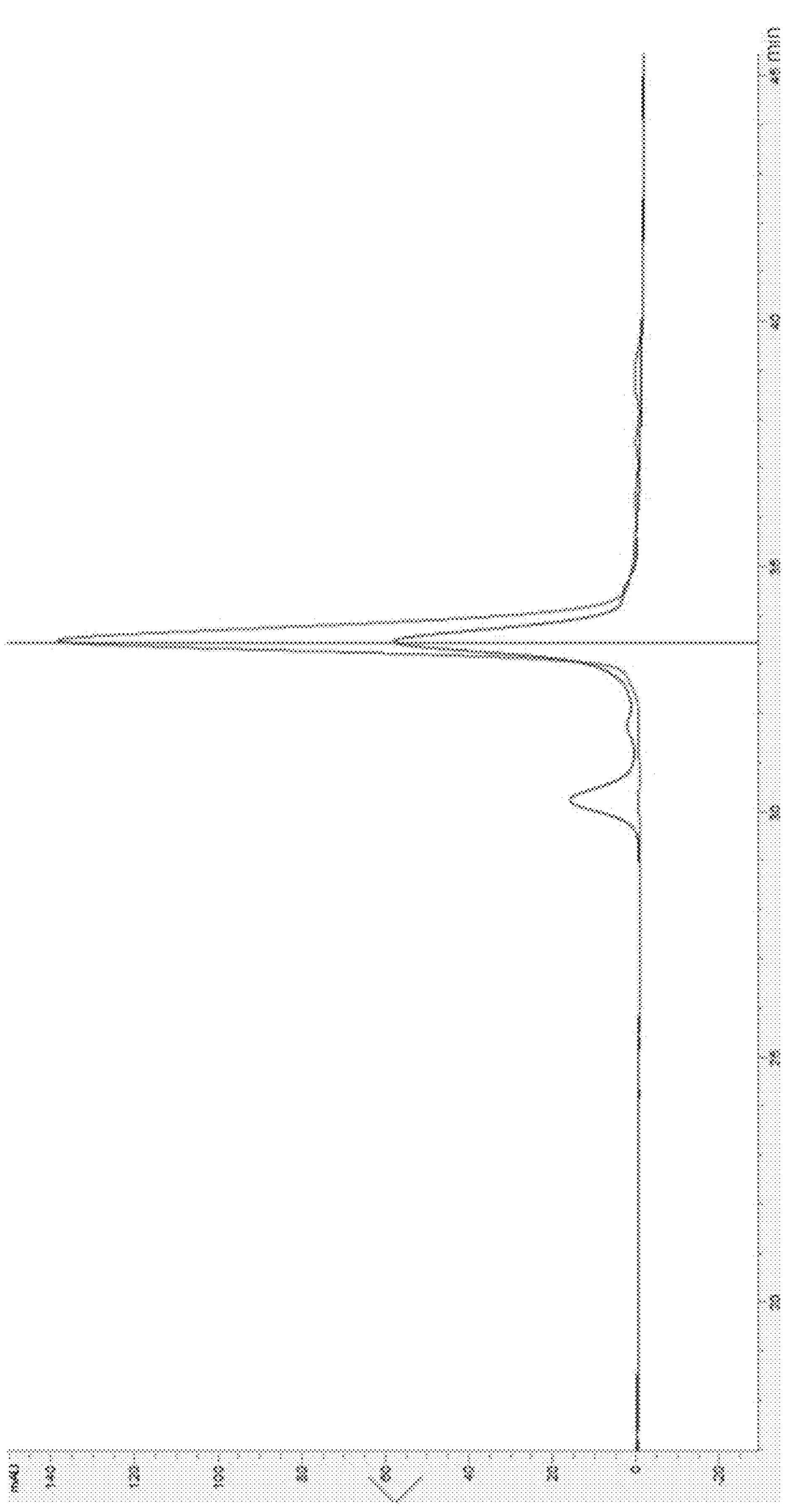
Figure 7:
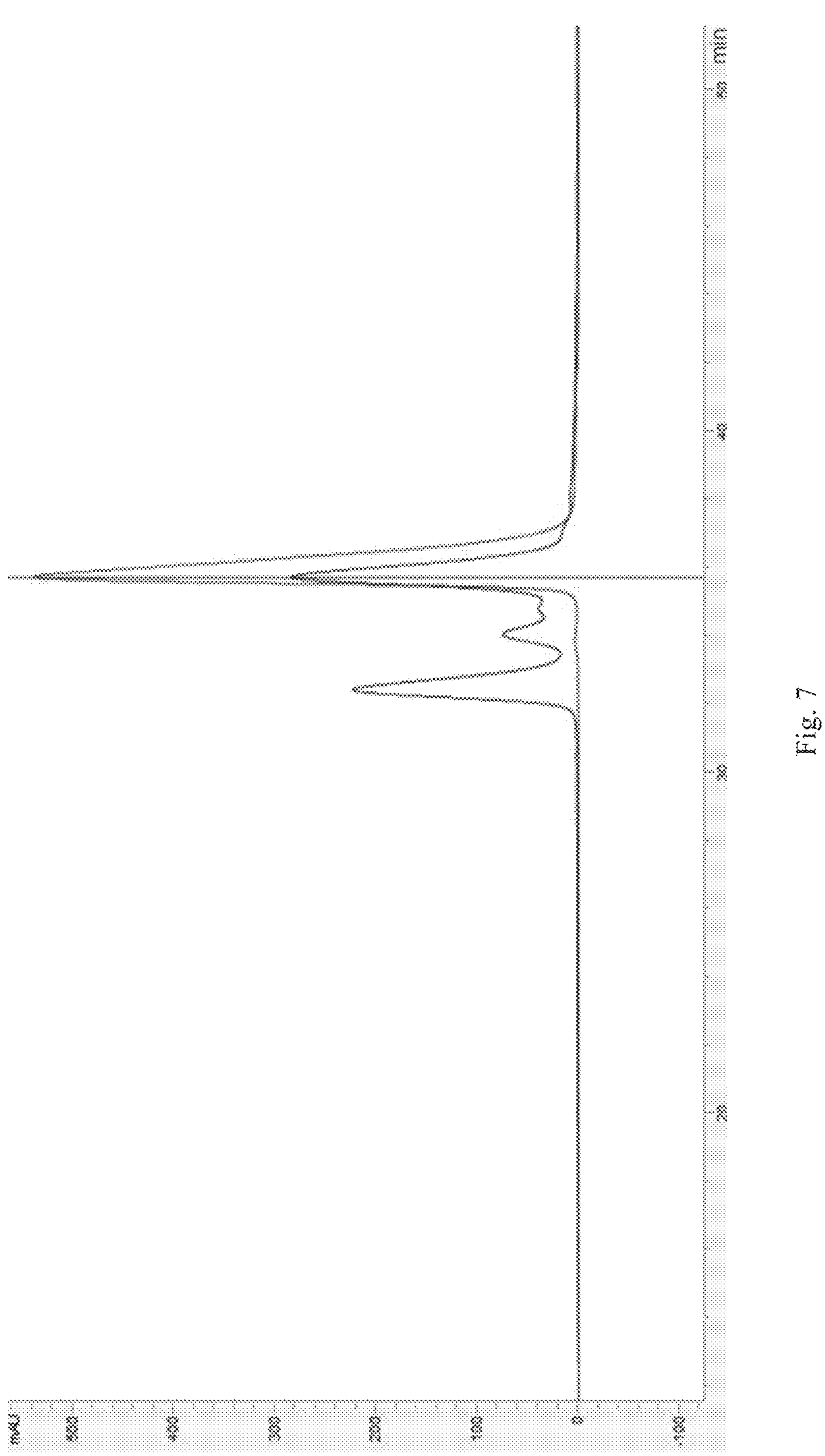
Figure 8:
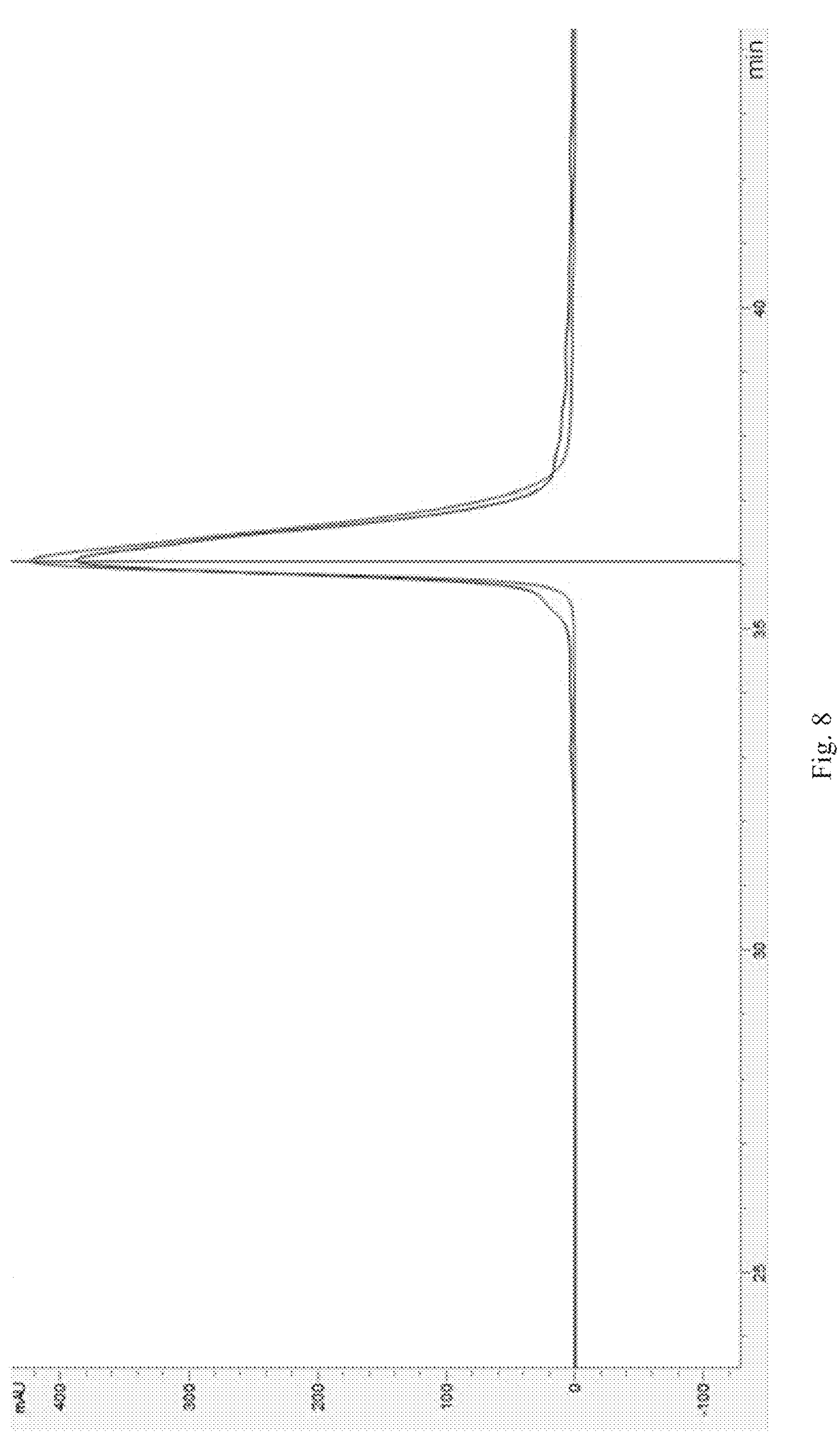
Figure 9:
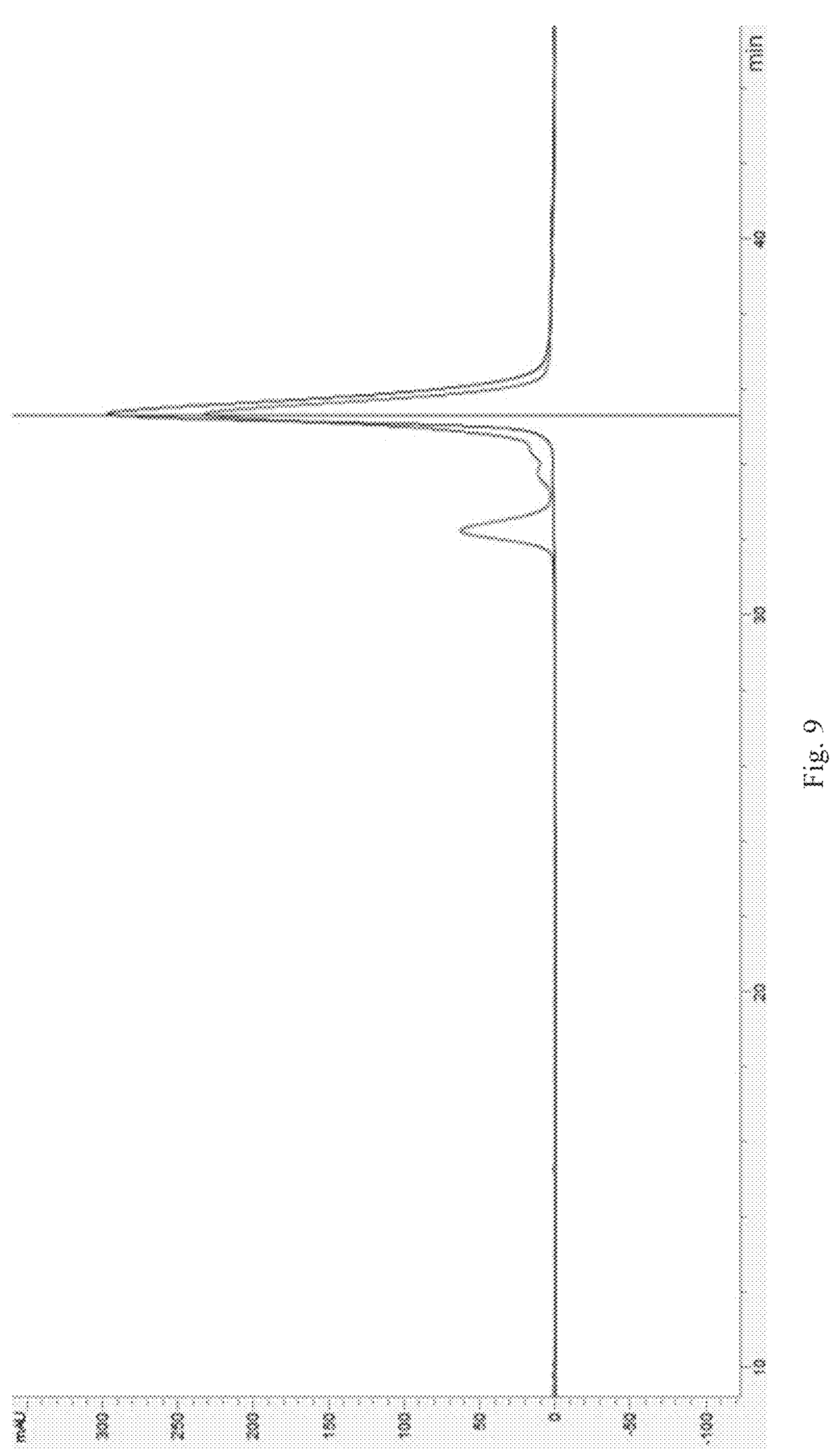
Figure 10:
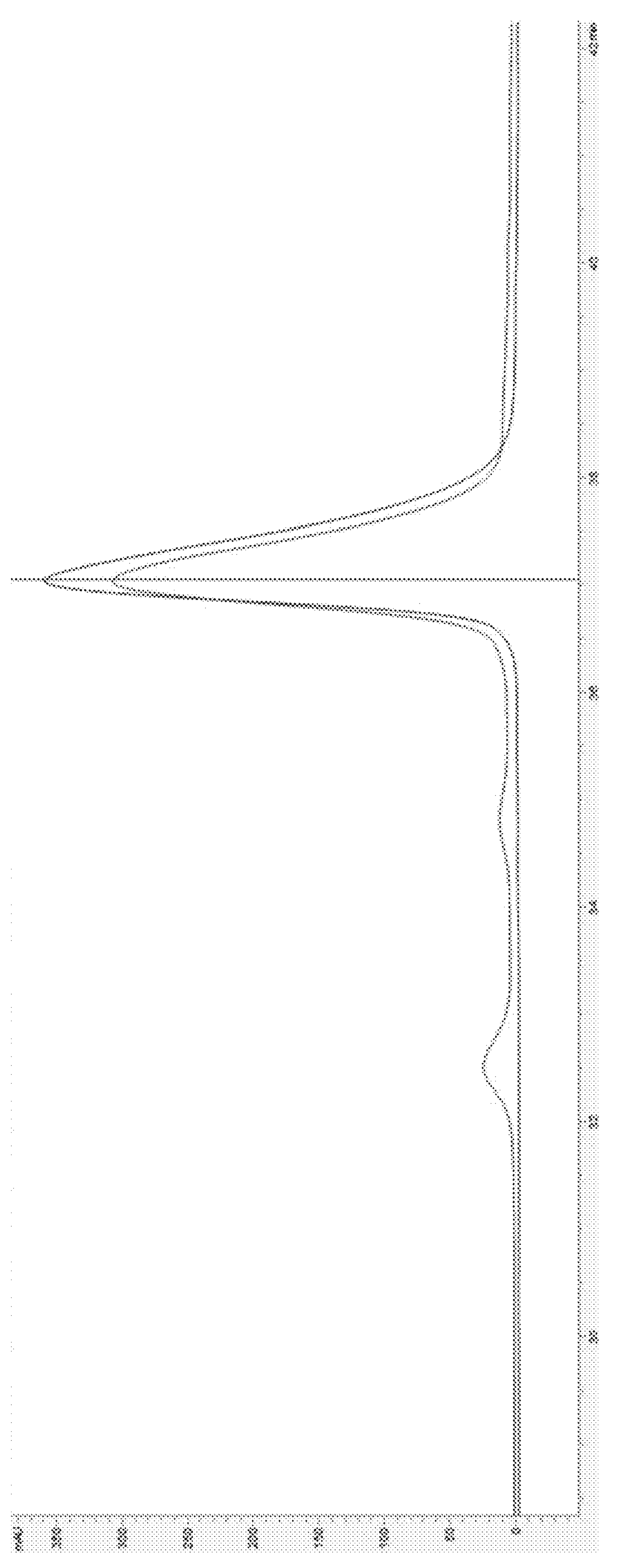

As shown in FIGS. 1-2, the molecular weight of IL29 mutant protein and the control are kDa respectively, indicating that the obtained target protein is correct, and only one band and no other impurity bands, indicating that the purity reaches 100%.

2.2 Detection of In Vitro Reversed-Phase High Performance Liquid Phase Purity of IL29 Mutant by Chromatographic Method 2.2.1 Reversed-Phase Liquid Chromatography The mobile phase A (acetonitrile:water:trifluoroacetic acid, in the volume ratio of 20:80:0.1) and the mobile phase B (acetonitrile:water:isopropanol:trifluoroacetic acid, in the volume ratio of 70:20:10:0.1) were prepared; and a chromatographic column (XBridge BEH C18 Column, 130A, 5 μm, 4.6 mm*100 mm) was used to analyze each test sample of proteins. The analytical conditions were as follows: flow rate 1.0 ml/min, acquisition time: 65 min, acquisition wavelength 214 nm, column temperature 45° C., and elution gradient as shown in Table 1 below.

TABLE 1

| Time (min) | 0 | 5 | 5.01 | 45 | 55 | 55.01 | 65 |
|---|---|---|---|---|---|---|---|
| B % | 27 | 27 | 27 | 49 | 70 | 27 | 27 |

Two injections of stock solution of a test sample were loaded in parallel, and the loading volume was set as15 μg-20 μg according to the sample concentration; finally, the purity of the main peak of the test sample was calculated by integrating according to the area normalization method.

2.2.2 Ion Exchange Chromatography

The mobile phase A (25 mmol/L phosphate buffer, pH 7.0) and mobile phase B (25 mmol/L phosphate buffer, 0.5 mol/L sodium chloride, pH 6.7) were prepared, and a chromatographic column (Thermo ProPac WCX-10 4.0*250 mm) was used to analyze each test sample of proteins. The analytical conditions were as follows: flow rate 0.8 ml/min, acquisition time: 55 min, acquisition wavelength 214 nm, column temperature 25° C., and elution gradient as shown in Table 2 below.

TABLE 2

| Time (min) | 0 | 30 | 31 | 40 | 41 | 55 |
|---|---|---|---|---|---|---|
| A % | 80 | 70 | 10 | 10 | 80 | 80 |
| B % | 200 | 30 | 90 | 90 | 20 | 20 |

The loading volume was 20 μg, and the purity of main peaks of two parallel injections of a test sample was calculated according to the area normalization method.

2.3 Determination of In Vitro Cell Biological Activity of IL29 Mutant by Reporter Gene Method HEK293-ISRE-Luc cells (purchased from National institutes for Food and Drug Control) were allowed to grow adherently in complete culture medium. The cells were passaged at a ratio of 1:4, 2-3 times per week, growing in complete culture medium. The cultured cells were taken to discard the culture medium, and the cells were washed once with PBS and then digested and collected; and the cell suspension containing $3.5\times10^5$ to $4.5\times10^5$ cells per 1 ml was prepared with assay culture medium (BIBCO). The prepared samples of IL29 mutant protein and IL29 control were transferred into a 96-well plate that could be used for cell culture and read by chemiluminescent microplate reader (Molecular Devices), and 100 μl of sample was added to each well; then the above cell suspension was inoculated into the same 96-well plate, 100 μl for each well to incubate at 37° C. and 5% carbon dioxide for 19-23 hours. The supernatant in the 96-well plate was carefully sucked out, and cell lysate and luciferase substrate were added according to the instructions of Luciferase Assay Kit (Bright-GloTM Luciferase Assay System, Promega), a chemiluminescence microplate reader was used to perform the assay, and the EC50 values of IL29 mutant and IL29 control were recorded separately. The relative biological activity was calculated as follows: the IL29 control was used as the standard, and the 0-point activity was defined as "100%"; and the relative biological activity=IL29 control EC50 (0-point)/IL29 mutant EC50.

The EC50 of each test sample of an IL29 mutant was determined, using IL29 control as the control, and the relative biological activity of each mutant was calculated. The specific results are shown in Table 3 below.

TABLE 3

In vitro cell biological activity data of IL29 mutants

| Protein types | $EC_{50}$ (ng/ml) | Relative biological activity (%) |
|---|---|---|
| IL29 control | 4.783 | 100% |
| IL29DE | 1.697 | 282% |
| IL29DS | 4.316 | 90% |
| IL29GA | 5.264 | 91% |
| IL29CS | 4.639 | 103% |
| IL29DE + CS | 1.428 | 335% |
| IL29DS + CS | 4.982 | 96% |
| IL29GA + CS | 3.985 | 120% |

As can be seen above, although the D at position 162 of IL29 is not located at the active center for IL29 receptor binding, it was unexpectedly found that the EC50 of single-point mutant IL29DE is only 1.697, which is much lower than that of IL29 control (4.783), and the biological activity is surprisingly increased by nearly three times, while the other single-point mutants IL29DS, IL29GA and IL29CS show essentially no change in EC50/biological activity as compared with IL29 control. Double-point mutant IL29DE+CS has a mutation from C to S at position 166 in addition of the single-point mutant IL29DE, and its biological activity is further improved relative to the single-point mutant II . . . 29DE, but the biological activities of the double-point mutants IL29DS+CS and IL29GA+CS are not significantly improved as compared with the IL29 control. The present results suggest that the mutation from D to E at position 162, which is not located at the active center for IL29 receptor binding, has the unexpected effect of improving the biological activity of the mutated protein.

Example 3: Detection Results of Stability of IL29 Mutants at 50° C.

The stability of the proteins in this application was mainly characterized by reversed-phase high performance liquid phase purity.

Under the conditions of 50° C.±2° C./75% relative humidity+5% relative humidity, samples were taken according to Table 4, the reversed-phase high performance liquid phase purity of each test sample of IL29 mutants was determined by the same method in 2.2.1 of Example 2, and the biological activity of each test sample of IL29 mutants was determined by the same method in 2.3 of Example 2. The details are shown in Table 5, while the purity values at day 0 and 14 in Table 5 were used to make contrast chromatogram, as shown in FIGS. 3-10.

TABLE 4

Validation regimen on stability of IL29 mutants at 50° C.

| | |
|---|---|
| Test condition | 50° C. ± 2° C./75% relative humidity ± 5% relative humidity |
| Sampling time | Day 0, 7, and 14 |
| Test items | 1. Reversed-phase HPLC purity; 2. Biological activity |

TABLE 5

Detection results of reversed-phase HPLC purity of IL29 mutants at 50° C.

| Protein types | Main peak (%) | | | Reduction on Day 14 as |
|---|---|---|---|---|
| Sampling time point | Point 0 | Day 7 | Day 14 | compared with Point 0 (%) |
| IL29 control | 85.82 | 56.70 | 34.46 | 51.36 |
| IL29DE | 92.68 | 89.35 | 77.39 | 15.29 |
| IL29DS | 91.87 | 86,25 | 67.65 | 24.22 |
| IL29GA | 89.45 | 85.82 | 69.80 | 19.65 |
| IL29CS | 97.03 | 64.66 | 46.20 | 50.83 |
| IL29DE + CS | 97.22 | 93.62 | 86.66 | 10.56 |
| IL29DS + CS | 95.11 | 90.79 | 76.86 | 18.25 |
| IL29GA + CS | 96.79 | 89.96 | 81.82 | 14.97 |

It can be seen from the results in Table 5 and FIGS. 3-10 above that, the two test samples with the greatest decrease in purity are IL29 control and IL29CS, wherein the purity of IL29 control drops sharply from 85.82% to 34.46% in 14 days with a decreasing amplitude of up to 51.36%, and the purity of IL29CS drops sharply from 97.03% to 46.20% in 14 days with a decreasing amplitude of up to 50.83%; the two test samples with the smallest decrease in purity are IL29DE and IL29DE+CS, wherein the purity of IL29DE drops from 92.68% to 77.39% in 14 days with a decreasing amplitude of only 15.29%, and the purity of IL29DE+CS drops from 97.22% to 86.66% in 14 days with an even lower decreasing amplitude of only 10.56%. The decrease in purity of the other single-point mutants IL29DS and IL29GA in 14 days is 24.22% and 19.65%, respectively, and the decrease in purity of the other double-point mutants IL29DS+CS and IL29GA+CS in 14 days is 18.25% and 14.97%, respectively.

It can be inferred from the above results that, the single point mutant with the mutation from D to E at position 162 (IL29DE) has the best stability and the least decrease in purity in 14 days. Moreover, since the stability of IL29CS is much less than that of IL29DE, the stability of the double-point mutant IL29DE+CS might be lower than that of IL29DE according to conventional inference, however, the stability of IL . . . 29DE+CS in the present application is still much higher than that of IL29DE, indicating that these two points mutated at the same time also bring a synergistic effect in improving the stability of the mutant. The biological activity of the mutants was also measured and found to be basically unchanged in 14 days for both mutants IL29DE and IL29DE+CS.

Example 4: Detection Results of Light Stability of IL29 Mutants at 25° C.

The stability of IL29 mutants was detected under the condition 25° C.±2° C./60% relative humidity ±5% relative humidity/5000±500 lux, samples were taken according to Table 6, and the same method in Example 2 was used to detect the stability of IL29 mutants. The results are shown in Table 7, wherein IL29 CS was used as the control.

TABLE 6

Detection regimen on light stability of IL29 mutants at 25° C.

| | |
|---|---|
| Test condition | 25° C. ± 2° C./60% relative humidity ± 5% relative humidity/5000 ± 500 lux |
| Sampling time | Day 0, 5, and 10 |
| Test items | Appearance, reversed-phase HPLC purity, and ion exchange purity |

TABLE 7

Detection results of light stability of IL29 mutants at 25° C.

| Sampling time | | Reversed-phase HPLC purity (%) | | Ion exchange purity (%) | |
|---|---|---|---|---|---|
| (day) | Appearance | IL29DE + CS | IL29CS | IL29DE + CS | IL29CS |
| 0 | Clear, colorless, transparent | 95.10 | 95.361 | 93.26 | 97.00 |
| 5 | Clear, colorless, transparent | 93.16 | 90.756 | 90.99 | 89.28 |
| 10 | Clear, colorless, transparent | 91.72 | 84.30 | 86.55 | 77.14 |

It can be seen from the above results that, the light stability of IL29 mutant IL29DE+CS is better than that of IL29 CS under the 25° C. light illumination condition.

Example 5: Nebulization Stability Tests of Each IL29 Mutant

Figure 11:
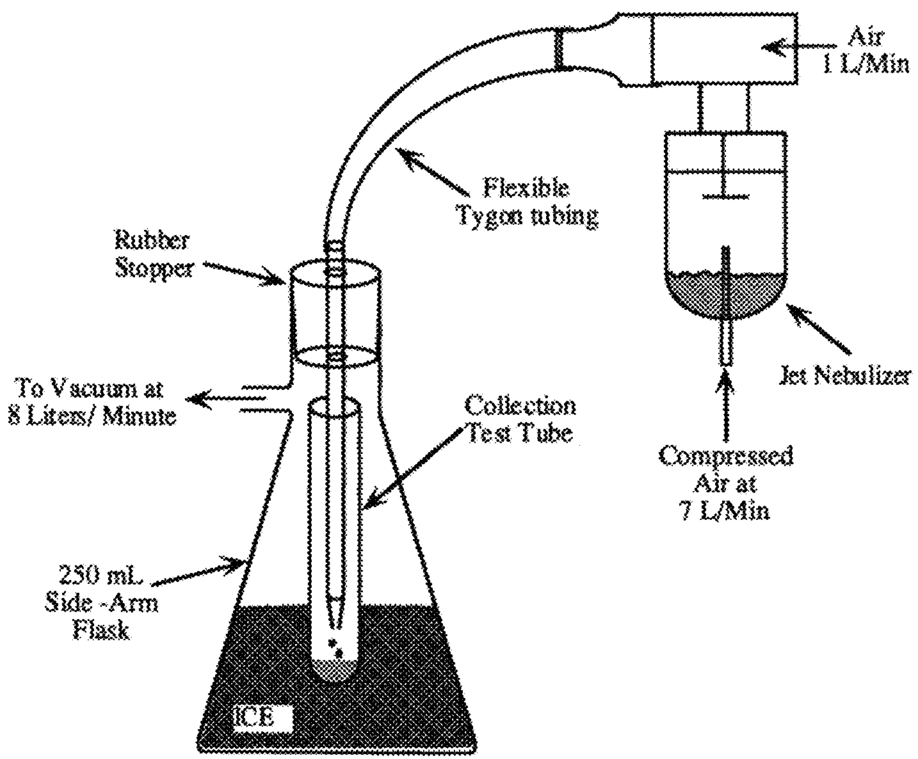
FIG. 11 shows a diagram of the aerosol collection apparatus in the nebulization stability assay on IL29 mutants.

A jet nebulizer of PARI LCD type and TurboBOY N nebulizer pump from Germany were used for nebulization tests. 2 ml of sample was nebulized, and aerosol was collected in the manner below according to FIG. 11; as for the collected sample, the purity of each test sample of IL29 mutants was detected according to the same method as in Example 2.2.1 by reversed-phase high performance liquid phase, thereby verifying the nebulization stability of each mutant. Particularly, IL29 CS was used as the control, and the results are shown in Table 8 below.

TABLE 8

Detection results of nebulization stability of IL29 mutants

| Protein sequence type | Reverse-phase purity before and after nebulization: Before nebulization | After nebulization | Difference between purity before and after nebulization |
|---|---|---|---|
| IL29CS | 96.65% | 85.26% | 10.39% |
| IL29 DE + CS | 95.12% | 92.05% | 3.07% |
| IL29 GA + CS | 94.24% | 91.13% | 3.11% |
| IL29 DS + CS | 93.41% | 85.31% | 8.1% |

It can be seen from the results in the above table that, the purity of IL29 mutants IL29 DE+CS and IL29 GA+CS decreases only about 3% after nebulization, and the purity of IL29 DS+CS decreases 8.1% after nebulization; while the purity of IL29CS decreases greatly after nebulization, surprisingly decreasing by nearly 11%. It can be seen that, the nebulization stability of double-point IL29 mutants is significantly enhanced as compared with IL29CS, especially IL29 mutants IL29 DE+CS and IL29 GA+CS have particularly good stability after nebulization, and are particularly suitable for the preparation of aerosol inhalation formulations.

Example 6: In Vitro Efficacy Assay of IL29 Mutant on RSV-Infected Human Bronchial Epithelial Cells (HBEC)

After cell differentiation (Cell Application) of HBECs (human bronchial epithelial cells) was completed, serial diluted IL29 mutant (IL29 DE+CS), and a positive control drug (BMS-433771, provided by Wuxi AppTec, Shanghai, China; a respiratory syncytial virus fusion protein inhibitor) were respectively added to the differentiated HBEC cells, culturing at 37° C. and 5% $CO_2$ in an incubator. The HBEC cells were treated with drugs (serial diluted IL29 mutant (IL29 DE+CS), or a positive control drug) 24 h prior to infection, and 1 h and 24 h post infection by respiratory syncytial virus (provided by Wuxi AppTec). RSV with a titer of 100, TCID50 (half of the infective dose of tissue culture) was added to each of the activity test wells, culturing the cells in 37° C. and 5% $CO_2$ incubator for 3 days, then RSV RNA was extracted from the cells by using the RNA Extraction Kit (Catlog: 74181, Qiagen), and quantified by RT-qPCR. The compound dose-response curves were analyzed and EC50 values and average inhibition rates were calculated by using GraphPad Prism software, and the results are shown in Table 9 and Table 10.

TABLE 9

Inhibition of RSV infection by positive control drug BMS-433771 in HBEC cell model

| Result: Drug No. | Drug name | $EC_{50}$ (nM) | Average inhibition rate (%) (nM): 1250 | 250 | 50 | 10 |
|---|---|---|---|---|---|---|
| 1 | BMS-433771 | 213.10 | 97.91 | 85.31 | 29.30 | 31.65 |

TABLE 10

Inhibition of RSV infection by IL29 mutants in the HBEC cell model

| Result: Drug No. | Drug name | $EC_{50}$ (ng/ml) | Average inhibition rate (%) (ng/ml): 1000.0 | 100.0 | 10.0 | 1.0 |
|---|---|---|---|---|---|---|
| 2 | IL29DE + CS | 0.13 (6.5 pM) | 71.50 | 100.00 | 94.90 | 78.97 |

The results indicate that IL29 DE+CS shows good anti-RSV efficacy in the in vitro model of human bronchial epithelial cells with an EC50 of 0.13 ng/ml (6.5 pM), which is 1/100000 of the control drug and significantly lower than the control drug.

Example 7: In Vivo Efficacy Assay of IL29 Mutant in RSV-Infected Mouse Model

On day 0, all mice (female, 6-7 weeks old, 16-18 g, specific pathogen-free (SPF) grade BALB/c mice (provided by Wuxi AppTec, Shanghai, China)) were anesthetized by intraperitoneal injection of sodium pentobarbital (75 mg/kg), and inoculated by nasal drip with RSV (human respiratory syncytial virus A2, RSV-A2; purchased from BEI Resources, NIAID, NIHBethesda, MD) at an inoculated dosage of 1.1×105 PFU per animal, and the inoculating volume is 50 μL.

Figure 12:
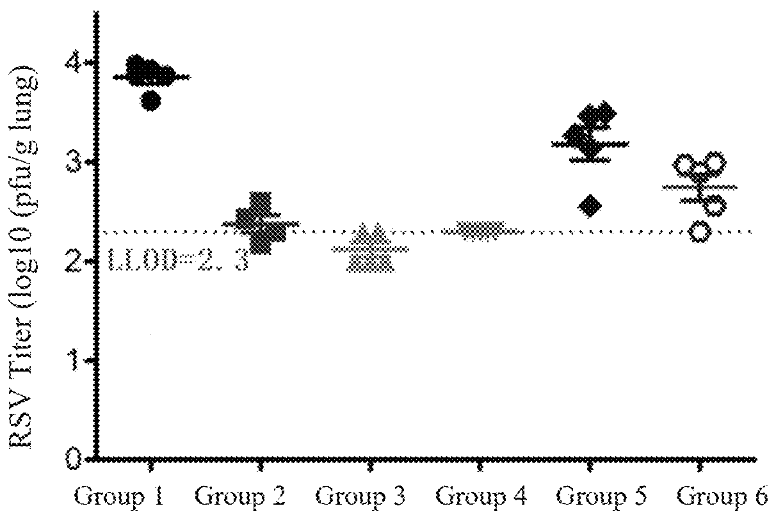
FIG. 12 shows the in vivo efficacy results of ribavirin and IL29 mutants by different dosing regimens in a mouse model of RSV infection.

From day 0 to day 3, the animals were administered according to the regimen in Table 11, and administration method was to spray into lungs. After mice were anesthetized, the micro spray nozzle cannula of a liquid nebulizer device (purchased from Shanghai Yuyan Instruments Co., Ltd.) preloaded with the drug solution was gently inserted into the appropriate position in the trachea of the mice, rapidly pressing the piston of the nebulizer high-pressure push device to nebulize a quantitative volume of the drug into the lungs of the mice at a frequency of once daily (referring to the dosing regimen in pages 13-33 of Joseph D. Brain, Dwyn E. Knudson, Sergei P. Sorokin, Michael A. Davis, Pulmonary distribution of particles given by intratracheal instillation or by aerosol inhalation, Environmental research 11, Volume 11, Issue 1, 1976). The endpoint of the in vivo test was day 5 post infection, all animals were euthanized to collect the lung tissues, and viral titers in them were tested (plaque tests). The results are shown in Table 12 and FIG. 12.

TABLE 11

In vivo dosing regimen in mice

| Group | Number of animals/ group | Virus and infecting route | Inoculating dosage (/mouse) | Drug | Dosage | Dosing volume | Time point for first dosage | Admini-stration mode | Admini-stration cycle | Observation |
|---|---|---|---|---|---|---|---|---|---|---|
| 1 | 5* | Rsv-a2 , intranasal infection | $1.1 \times 10^5$ pfu, 50 μl | Saline | 0 | 50 μl | 1 h before inoculation | Nebulization | On day 0-3, once per day | On day 0-4, body weight was recorded and mice were observed for health status each day. |
| 2 | 5* | | | Riboviron | 50 mg/kg | 50 μl | 1 h before inoculation | Nebulization | On day 0-3, once per day | |
| 3 | 5* | | | Il29 mutant | 10 μg | 50 μl | 1 h before Inoculation | Nebulization | On day 0-3, once per day | |
| 4 | 5* | | | Il29 mutant | 10 μg | 50 μl | 1 h after inoculation | Nebulization | On day 0-3, once per day | |
| 5 | 5* | | | Il29 mutant | 10 μg | 50 μl | 24 h after inoculation | Nebulization | On day 1-3, once per day | |
| 6 | 5* | | | Il29 mutant | 1 μg | 50 μl | 24 h after inoculation | Nebulization | On day 1-3, once per day | |

Note:
The IL29 mutant used in this Example is IL29 DE + CS.

TABLE 12

In vivo efficacy results of different drugs in RSV-infected mouse model

| Group | RSV titer in lung tissue log10 (pfu/g lung) (Mean ± SEM) | Difference between the mean values (compared with the vehicle group) |
|---|---|---|
| 1 | 3.854 ± 0.063 (N = 5) | 0 |
| 2 | 2.376 ± 0.091 (N = 4) | 1.479** |
| 3 | 2.120 ± 0.073 (N = 5) | 1.736*** |
| 4 | 2.300 ± 0.000 (N = 5) | 1.556*** |
| 5 | 3.185 ± 0.168 (N = 5) | 0.672** |
| 6 | 2.745 ± 0.135 (N = 5)# | 1.112** |

Note:
* $P < 0.001$ and  $P < 0.01$, as compared with the vehicle (saline) group The data indicate that, RSV can replicate in large numbers in mice after inoculation, and the positive control drug ribavirin significantly inhibits RSV replication in mice, showing the expected in vivo anti-RSV activity and demonstrating the validity of this model system. The time point of ribavirin administration is 1 h prior to virus infection (prevention model), while the test drug IL29 mutant significantly inhibits RSV virus replication in mice under the set assay conditions (administrating 1 h prior to virus infection, 1 h post virus infection, and 24 h post virus infection); particularly, in the first administration groups of 1 h prior to (10 μg) and 1 h post (10 μg) inoculation, the viral titers in the lung tissues of mice are below the lower limit of detection, showing excellent in vivo anti-RSV efficacy. The administration group of administrating 24 h post virus infection also shows good anti-RSV efficacy. The results of the prevention model with ribavirin administered 1 h prior to infection was comparable to the antiviral effect of the treatment model with the IL29 mutant administered 1 h post infection. This also fully demonstrates that the IL29 mutant has very good antiviral therapeutic potential.

Example 8: In Vivo Efficacy Assay of IL29 Mutant in RSV-infected Cotton Rat Model On day 0, all rats (cotton rats (*Sigmodon hispidus*), half male and half female rats, 5 weeks old, SPF grade (purchased from Envigo)) were anesthetized by intraperitoneal injection of sodium pentobarbital (75 mg/kg), and inoculated by nasal drip with RSV (human respiratory syncytial virus A2 (RSV-A2), purchased from BEI Resources, NIAID, NIHBethesda, MD) at an inoculating dosage of $1.1\times10^5$ PFU per animal with inoculateing volume of 50 μL.

From day 0 to day 3, animals were administered according to the assay regimen in Table 13, and the administration method was to spray into lungs at a frequency of once a day (referring to the dosing regimen in pages 13-33 of Joseph D. Brain, Dwyn E. Knudson, Sergei P. Sorokin, Michael A. Davis, Pulmonary distribution of particles given by intratracheal instillation or by aerosol inhalation, Environmental research 11, Volume 11, Issue 1, 1976). Bronchoalveolar lavage fluid (BALF) was collected by inserting a 3 ml syringe with a 22 G needle into the trachea to inject 2 mL of 0.9% saline into the lungs. The collected BALF was dispensed in sterile 1.5 mLEP tubes, placing on dry ice to be frozen and stored at −80° C. until the plaque assay analysis. The results are shown in Table 14 and FIG. 13.

TABLE 13

In vivo dosing regimen for cotton rats

| Group | Number of animals/ group | Virus and infecting route | Inoculating dosage (/rat) | Drug | Dosage | Time point for first dosage | Admini-stration mode | Admini-stration cycle | Observation |
|---|---|---|---|---|---|---|---|---|---|
| 1 | 10 | RSV-A2, intranasal infection | $1.1 \times 10^5$ pfu, 50 μl | Saline | 0 | l h before inoculation | Nebulization | On day 0-3, once per day | On day 0-4, rats were observed for health status each day. |
| 2 | 10 | | | Il29 mutant | 100 μg/kg (0.01 mg/ 50 μl/animal) | 1 h after inoculation | Nebulization | On day 0-3, once per day | |
| 3 | 10 | | | Il29 mutant | 30 μg/kg (0.003 mg/ 50 μl/animal) | 1 h after inoculation | Nebulization | On day 0-3, once per day | |

TABLE 13-continued

In vivo dosing regimen for cotton rats

| Group | Number of animals/ group | Virus and infecting route | Inoculating dosage (/rat) | Drug | Dosage | Time point for first dosage | Admini-stration mode | Admini-stration cycle | Observation |
|---|---|---|---|---|---|---|---|---|---|
| 4 | 10 | | | Il29 mutant | 10 μg/kg (0.001 mg/ 50 μl/animal) | 1 h after inoculation | Nebulization | On day 1-3, once per day | |

Note:
The IL29 mutant used in this Example is IL29 DE + CS.

TABLE 14

In vivo efficacy results of different drugs on RSV-infected cotton rat model

| Group | 1 | 2 | 3 | 4 |
|---|---|---|---|---|
| RSV titer in BALF log10 (pfu/ml) | 5.32E±02 | 8.90E±01 | 3.22E±02 | 7.83E±02 |
| Difference between mean values | 2.44 | 2.275 | 2.302 | 4.466 |
| P value | N/A | 0.009 | 0.186 | 0.129 |

Figure 13:
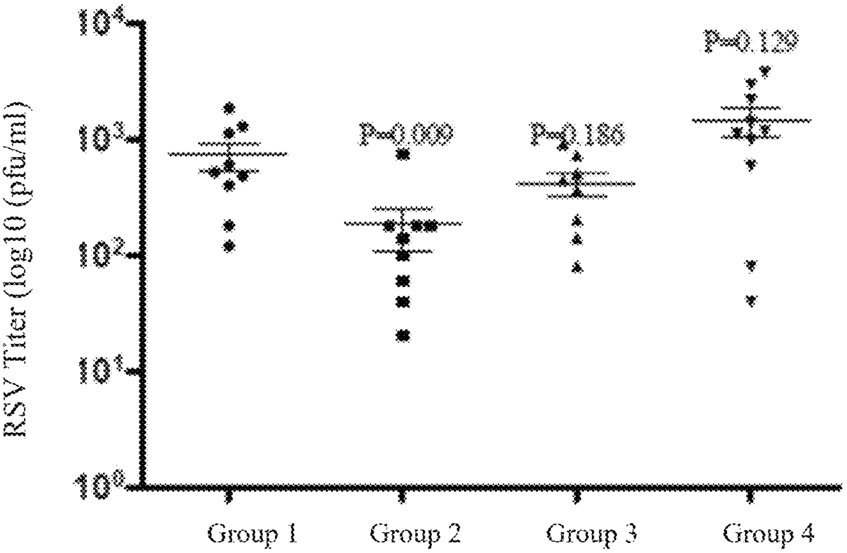
FIG. 13 shows the in vivo efficacy results of ribavirin and IL29 mutants by different dosing regimens in a cotton rat model of RSV infection.

The data in Table 14 and FIG. 13 show that, RSV can replicate in large numbers in cotton rats after inoculation, and the test drug IL29 mutant can significantly inhibit the replication of RSV virus in the rats under set conditions (treatment model, administering drug 1 hour after inoculation), and the virus titers in the bronchoalveolar lavage fluid of cotton rats in the groups (groups 2, 3 and 4) administrated with the first dosage (1 μg) of drug 1 hour after inoculation show statistical differences as compared with the control group, and the groups of the three doses (groups 2-4) show a dose dependence, indicating excellent in vivo anti-RSV efficacy. When cotton rats are infected with respiratory syncytial virus, the virus replicates heavily in the bronchi of their lungs, and the viral load of bronchoalveolar lavage fluid reflects very well the viral replication in the lungs. Thus, the IL29 mutant shows excellent therapeutic potential against respiratory syncytial virus.

Example 9: In Vitro Efficacy of IL29 Mutant Against Novel Coronavirus (2019-nCov)

200 μl of Vero E6 cells (African green monkey kidney cell line) at a concentration of $5\times10^4$ cells/ml were added to each well of a sterile 96-well culture plate, and cultured at 37° C., 5% $CO_2$ for 24 h. The test drug IL29 DE+CS was diluted to 100 ng/ml, 5 replicate wells were set up and 100 μl of drug solution was added to each well to incubate for 24 h. 100 μl per well of 100TCID50/ml titer of virus 2019-nCOV (stored at −80° C. by the Pathogen Center, Institute of Laboratory Animal Science, Chinese Academy of Medical Sciences, at a titer of $10^5TCID_{50}$/ml), blank control (vehicle control), and virus control (negative control) was added to incubate the cells in 37° C., 5% $CO_2$ incubator for 4-5 days; cytopathic effect (CPE) was observed under an optical microscope, a status of all cytopathic cells was recorded as "++++", 75% cytopathic cells was recorded as "++", 50% cytopathic cells was recorded as "++", 25% cytopathic cells was recorded as "+", and no cytopathic cells was recorded as "−".

The results show that, at 100 ng/ml (5 nmol/L) concentration of IL29 mutant, a status of no cytopathic cells is recorded as "−", wherein 100% of Vero E6 cells are protected from novel coronavirus, and IL29 mutant shows a very good effect against novel coronavirus (2019-nCov) infection.

Example 10: Efficacy Assay of IL29 Mutant Against Influenza Virus in Mice

Figure 14:
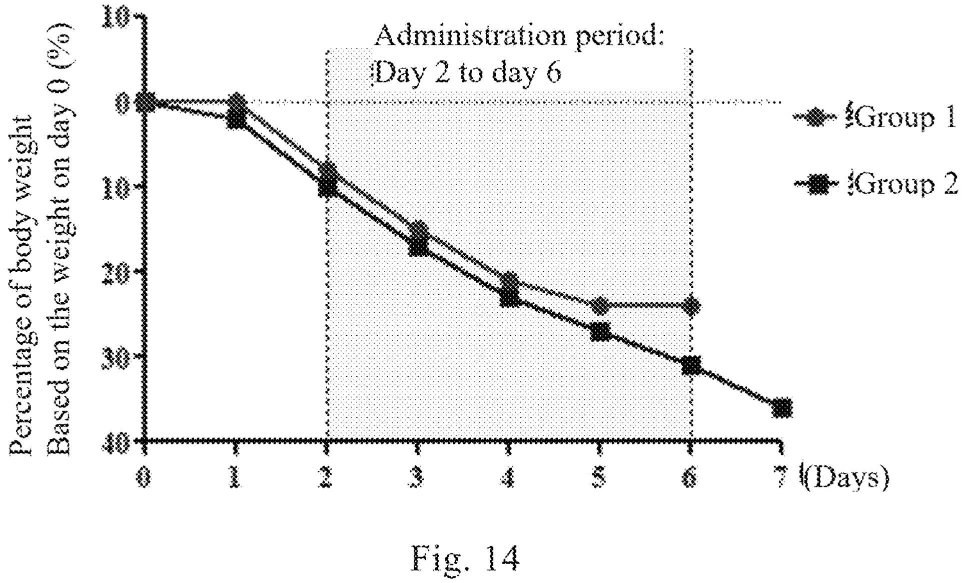
FIG. 14 shows the weight change of influenza virus-infected mice after treatment.
Figure 15:
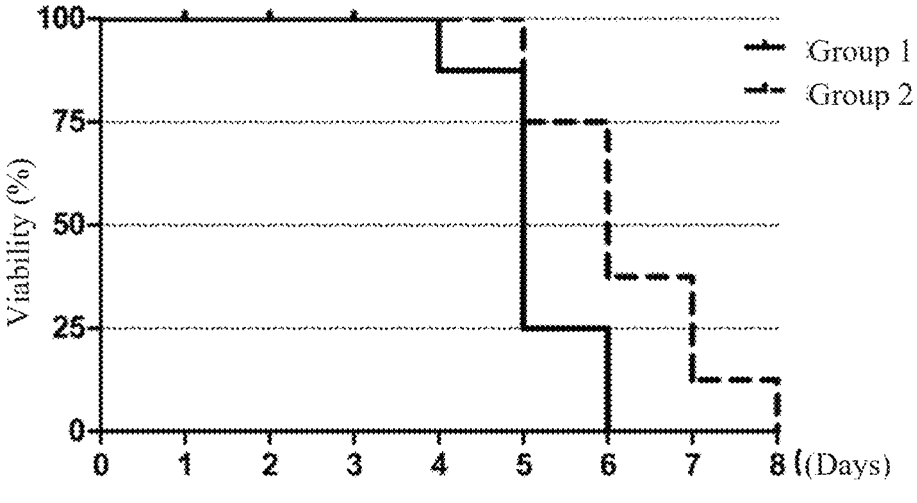
FIG. 15 shows the change of viability of influenza virus infected mice after treatment.
Figure 16:
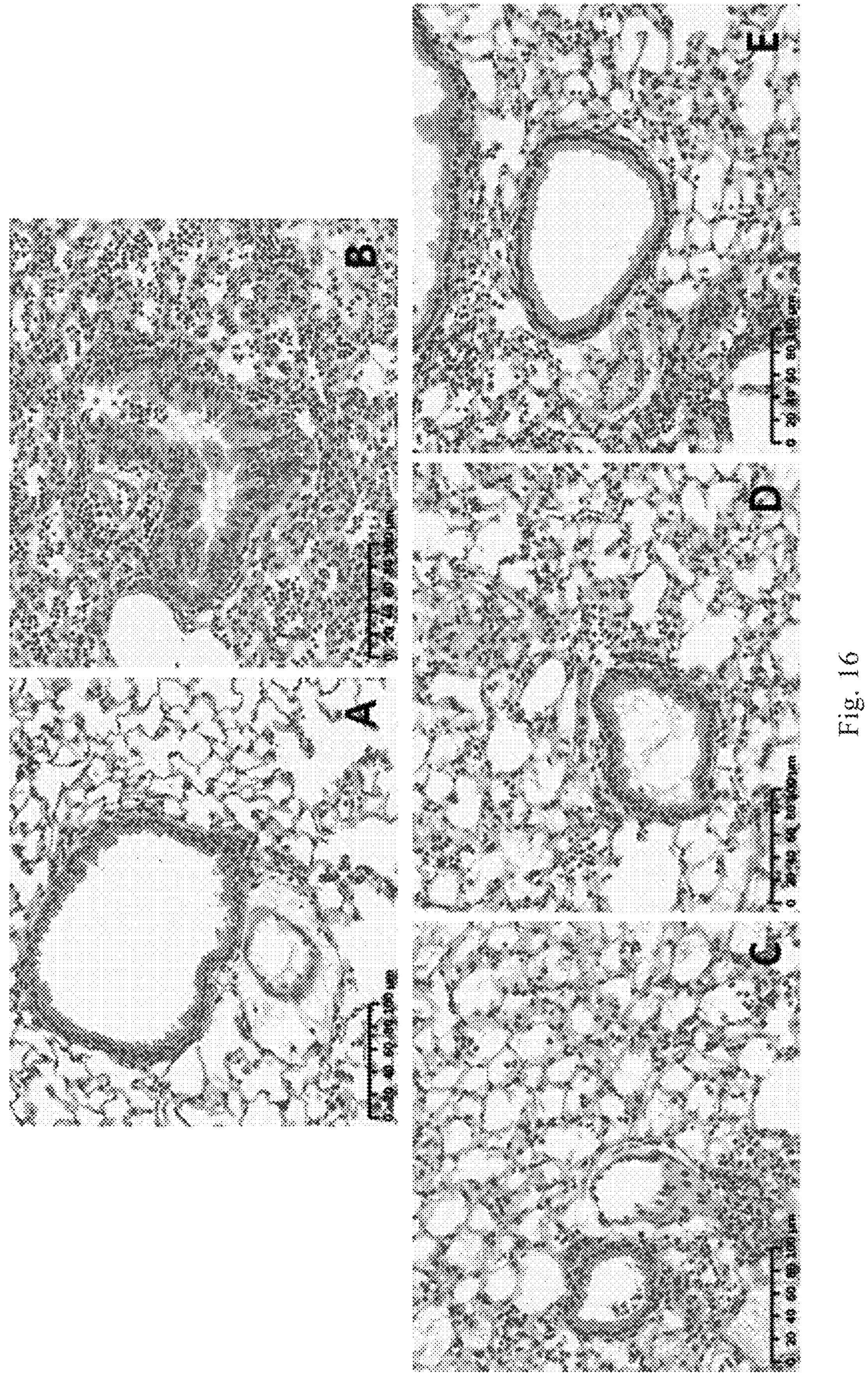
FIG. 16 shows the images about the pathological changes of injury of lung bronchiole and small pulmonary artery in mice, particularly, A: group 1; B: group 2; C: group 3; D: group 4; E: group 5.
Figure 17:
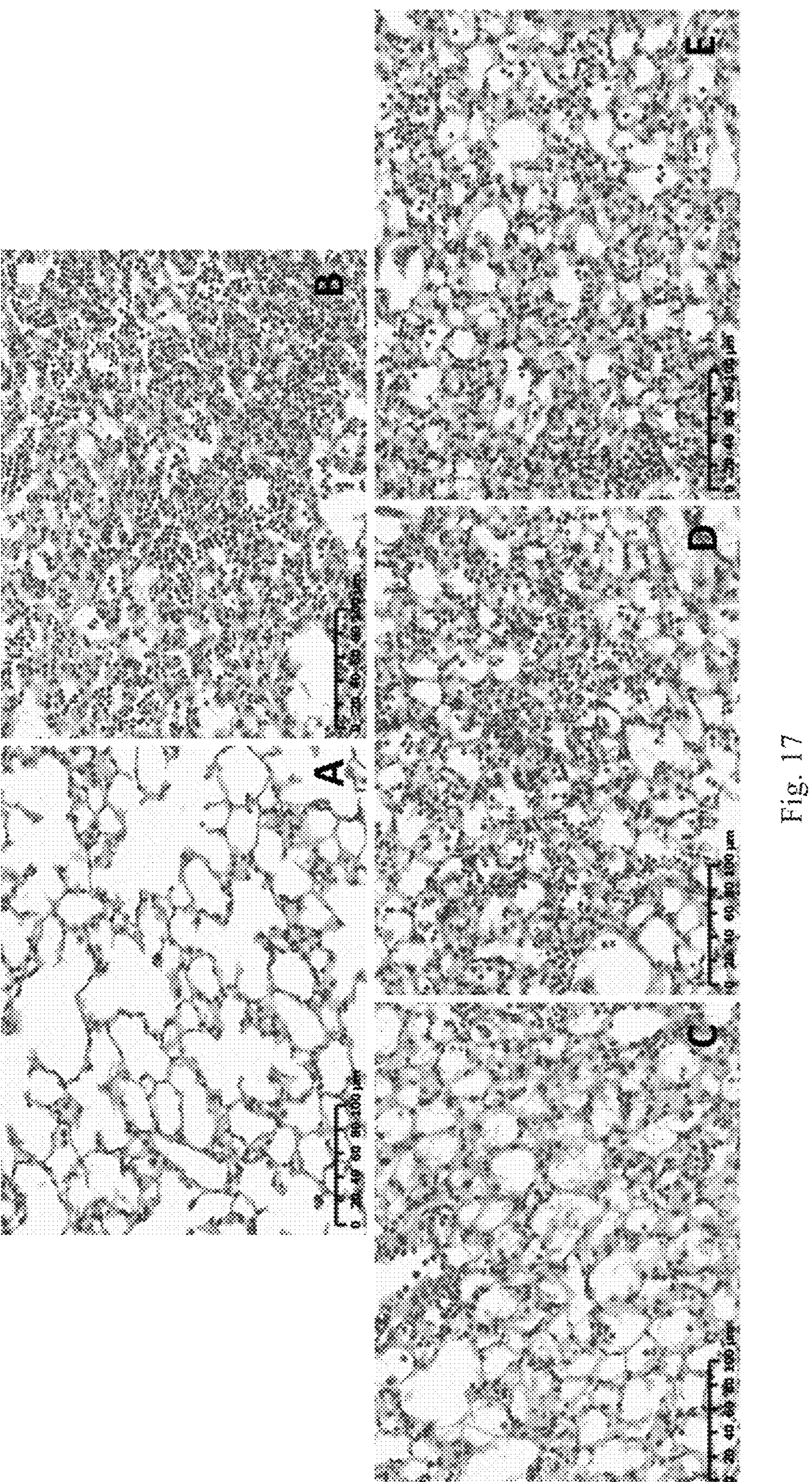
FIG. 17 shows the images about the pathological changes of alveolar injury in mice, particularly, A: group 1; B: group 2; C: group 3; D: group 4; E: group 5.
Figure 18A:
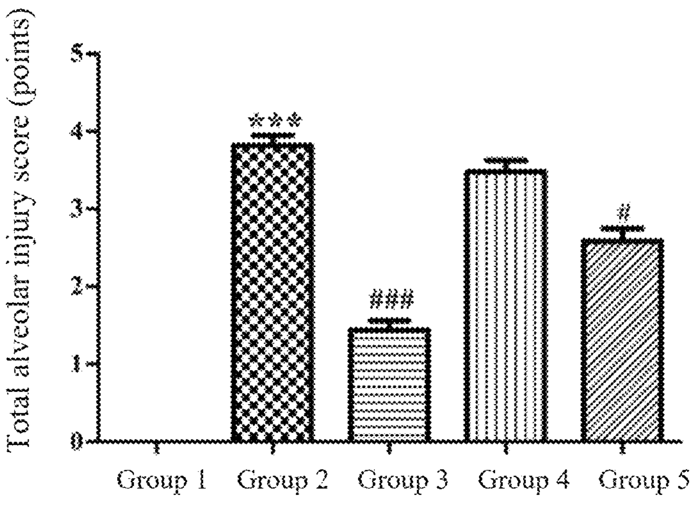
FIGS. 18*a-c* show the statistical graphs about the pathological scores of injury in each part of mouse lung, compared with group 1, ***P<0.001; compared with group 2, #P<0.05, ##P<0.01, ##P<0.001.
Figure 18B:
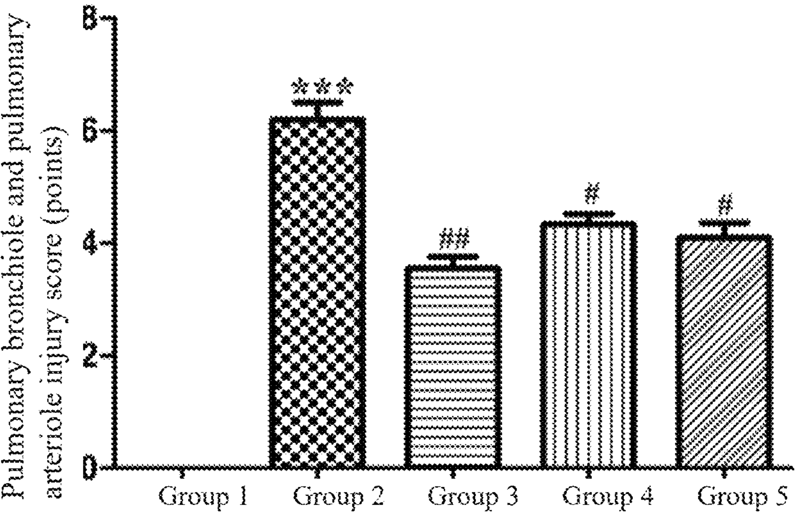
Figure 18C:
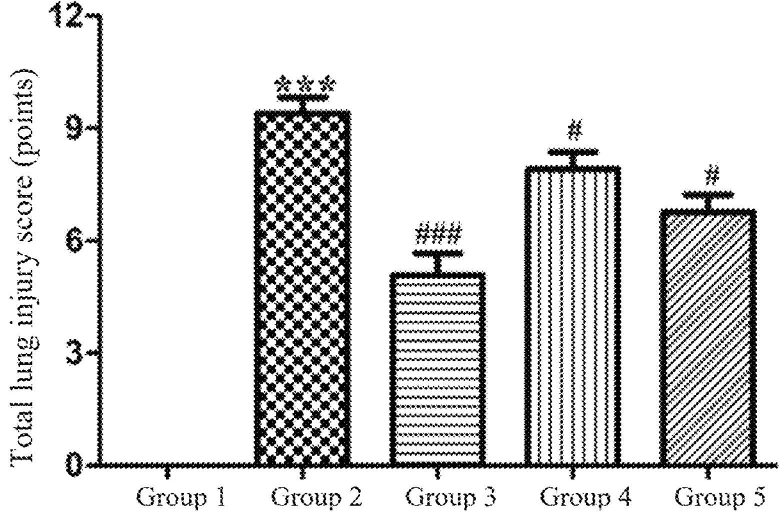

According to the dosing regimen in Table 15, the in vivo efficacy of influenza virus in BALB/c mice (provided by Shanghai Lingchang Biotechnology Co., Ltd.) was determined, with 8 mice in each group. The results are shown in FIG. 14 and FIG. 15.

TABLE 15

Regimen for determining the efficacy of IL29 mutant in influenza A virus in mice

| | | | Dosage regimen | | | | | | |
|---|---|---|---|---|---|---|---|---|---|
| Group | Test drug | Virus inoculation | Dosage (mg/kg) | Dosing volume (ml/kg) | Admini-stration mode | Dosing frequency | Time point for first dosage | Admini-stration cycle | Observation and results |
| 1 | Vehicle | Influenza A virus, WSN/33 (H1N1), 15000 pfu/mouse | 0 | 10 | Nasal drip | Once per day | 48 hours after virus inoculation | On day 2-6 | 1. Daily recording mouse weight. 2. Daily observing mice survival Results: The in vivo efficacy of the tested drugs was evaluated by body weight change and viability of the mice. |
| 2 | Il29 DE + CS | | 0.5 | 0.52 | | | | | |

It can be seen that, in a mouse infection model of influenza A virus WSN/33, when IL29 DE+CS is administered 48 hours post infection, the survival of infected mice is significantly prolonged and the mice are well protected.

Example 11: In Vivo Efficacy of IL29 DE+CS for Severe Respiratory Distress Syndrome Male C57 mice (18-22 g, 30 animals, Shanghai Lingchang Biotechnology Co., Ltd.) were anesthetized, and the trachea was exposed by cutting the skin; slowly injecting lipopolysaccharide LPS solution (50 μl/mouse, 0.3 mg/kg) via the trachea to replicate the model of acute lung injury; the animals' body weight and health status were monitored for a total of 24 h from the beginning of modeling to the end of assay.

According to the dosing regimen in Table 16, the efficacy of dexamethasone (DEX) and IL29 DE+CS in the mouse model of severe respiratory distress syndrome was determined. 24 h after modeling, mice were euthanized, and lung tissue was removed and fixed for subsequent pathological testing, and the results are shown in FIGS. 16-18*a-c*.

TABLE 16

Regimens for the in vivo efficacy assay of dexamethasone and IL29 DE + CS in the treatment of severe respiratory distress syndrome

| Grouping | Animal number | Model | Drug | Administration mode |
|---|---|---|---|---|
| Group 1 | 6 | No | Saline | Nebulization |
| Group 2 | 6 | Yes | Saline | Nebulization |
| Group 3 | 6 | Yes | DEX-3 mg/kg | Oral administration |
| Group 4 | 6 | Yes | IL29 DE + CS-240 μg/kg* | Nebulization |
| Group 5 | 6 | Yes | IL29 DE + CS-10 mg/kg | Subcutaneous administration |

*Group 4 was the nebulization group, and the nebulization was performed for 30 min at a drug concentration of 1 mg/ml. Animals were administered with drug before modeling, and administered again 12 h after modeling.

As can be seen, the study in the LPS-induced mouse acute lung injury model show that, in histological evaluation, compared with the model group, IL29 DE+CS nebulization and subcutaneous administration groups have significant efficacy in reducing lung injury and inflammatory response.

Example 12: Toxic Effects of IL29 Mutant on African Green Monkey Kidney Vero Cells In the Vero cell culture system, the toxicity of different concentrations of antibodies to Vero cells was determined by the CCK-8 assay.

Vero cells were inoculated into a 96-well culture plate at a concentration of 5000 cells/well, culturing until the cells formed a monolayer, then the culture medium was discarded, and the cells were washed twice with Hank's solution; the test drugs IL29 mutant IL29 DE+CS and Remdesivir were respectively diluted with MEM medium, at starting concentrations of 1000 nmol/L (19.6 μg/mL) and 50 μmol/L, diluting 3 times continuously to obtain 8 concentrations. Three replicate wells were set for each drug concentration, and 150 μL of drug solution was added to each well. At the same time, the Vero cell normal growth control well was set, and incubated at 37° C., 5% $CO_2$ incubator for 48 h. Then 15 μL of CCK-8 reagent was added to each well, and 3 hours later, the OD value at 450 nm was determined by using a microplate reader. The dose toxicity effect of the drugs on cells and the maximum non-toxic concentration were calculated, and the drug-cytotoxicity effect curve was plotted.

Figure 19:
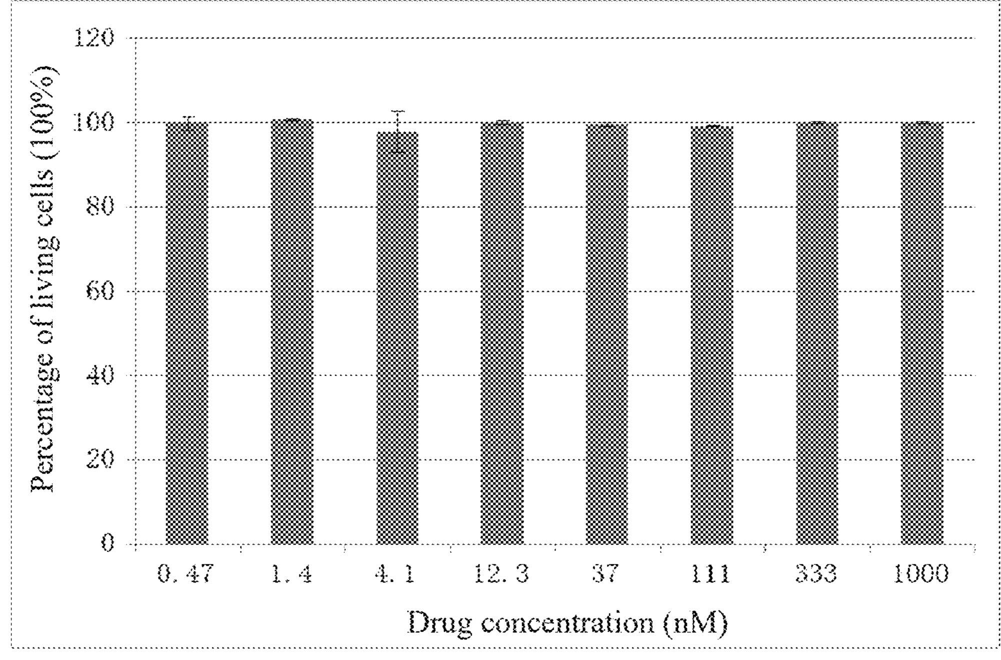
FIG. 19 shows the toxic effects of different concentrations of IL29 mutants on Vero cells.

The results show that, at the concentrations of 1000 nmol/L (19.6 μg/mL) and below, the tested drug IL29 DE+CS has no significant toxic effect on Vero cells, and the cell viability is greater than 90%; at the concentrations of 50 μmol/L and below, Remdesivir has no obvious toxic effect on Vero cells, and the cell viability is more than 90%. The tested drug IL29 DE+CS has $CC_{50}$>1000 nmol/L (19.6 g/mL), the details are shown in FIG. 19, and as for Remdesivir, $CC_{50}$>50 μmol/L.

Example 13: Inhibition of Novel Coronavirus by IL29 Mutant In Vitro

In Vero cell culture model, immunofluorescence assay and nucleic acid detection kit (fluorescent PCR method) were adopted to detect the preventive and treatment effects of different concentrations of IL29 mutant on novel coronavirus.

2.1 Preparation of Drug-Virus Mixture

Test group: the concentration of the test drug IL29 mutant IL29 DE+CS was started from the highest 100 ng/ml, serially diluted 5-fold with MEM medium containing 10% FBS to obtain samples of 7 concentrations, mixing with virus solution of novel coronavirus strain (deposited in the State Key Laboratory for Diagnosis and Treatment of Infectious Diseases, Zhejiang University, with $TCID_{50}$ of $10^{-5.5}$/mL) by the ratio of MOI=100.

Positive control group: Remdesivir positive control group was diluted with MEM medium containing 10% FBS to obtain 6 final concentrations of 10 μM, 3 μM, 1 μM, 0.3 μM, 0.1 μM, and 0.03 μM, then mixing with viral solution of novel coronavirus strain by the ratio of MOI=100.

In this test, a prevention model group and a treatment model group were set up, and Vero cells were pretreated for 24 h with different concentrations of the test drug IL29 DE+CS samples before mixing with virus in the above test groups as the in vitro prevention model group, and cells without pretreatment were used as the in vitro treatment model group.

2.2 Test Procedure

Vero cells were inoculated into 48-well culture plate at a concentration of 10,000 cells/well and cultured until the cells entered in logarithmic growth phase, dividing them into prevention group, test group, positive control group, negative control group (with virus solution only) and pure cell group (without virus), wherein 3 replicate wells were set for each sample.

The cell culture medium in the prevention group was sucked out, and different concentrations of the test drug IL29 DE+CS samples were added, 500 μL per well, the rest of the cells were not treated, culturing the cells at 37° C., 5% $CO_2$ for 24 h. Then the cell culture medium in all four groups was sucked out, and the drug-virus mixture prepared above was added correspondingly, and the insufficient volume in the negative control and pure cell groups was complemented with culture medium, culturing at 35° C. and 5% $CO_2$ in an incubator for 3 h; then the cell culture medium was sucked out, and the cells were washed with PBS before adding the corresponding concentration of 500 μL drug diluent to each well, and cultured in an incubator at 35° C. and 5% $CO_2$ for 48 h.

2.2.1 Novel Coronavirus Nucleic Acid Detection

200 μL of culture supernatant was taken to extract the nucleic acid by using a magnetic bead extraction kit (MVR01, Liferiver Bio-Tech Corp.) and an automatic nucleic acid extractor (EX3600, Liferiver Bio-Tech Corp.), and the final elution volume was 50 μL. 5 μL of the nucleic acid extract was taken to detect the nucleic acid level of the virus by using the One-step novel coronavirus nucleic detection kit (fluorescent PCR method, item No. Z-RR-0479-02-50, CFDSM 20203400057, Liferiver Bio-Tech Corp.).

Figure 20:
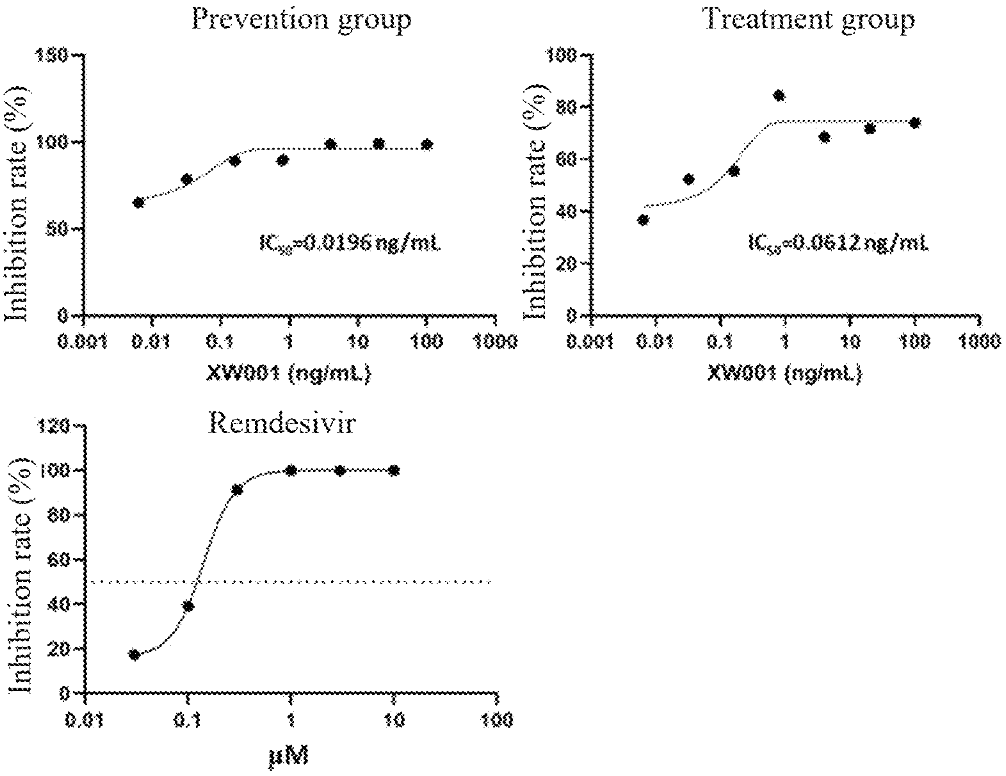
FIG. 20 shows the inhibition levels of novel coronavirus in the prevention group, treatment group and positive control group.

The results are expressed in terms of Ct values. The corresponding relation between Ct value and virus copy number is: y=−3.33x+48.69, wherein y is the Ct value, and x is the logarithm of the number of viruses with a base of 10. The inhibition rate is calculated by the following formula: Inhibition rate=[1-10^((y$_{virus\ control}$−y)/3.33)]×100%. The results of the tests are shown in Table 17 and FIG. 20 below.

TABLE 17

Detection results of inhibition rate against novel coronavirus in each group

| Treatment | Concentration | Ct Value 1 | Ct Value 2 | Ct Value 3 | Ct Value Mean | Average inhibition rate (%) |
|---|---|---|---|---|---|---|
| Prevention group | 100 ng/ml | 23.62 | 24.43 | 22.40 | 23.48 | 98.4746 |
| | 20 ng/ml | 24.62 | 23.37 | 24.20 | 24.07 | 99.0766 |
| | 4 ng/ml | 22.76 | 24.34 | 23.89 | 23.66 | 98.6755 |
| | 0.8 ng/ml | 20.68 | 20.34 | / | 20.51 | 89.4635 |
| | 0.16 ng/ml | 20.30 | 20.43 | 20.63 | 20.45 | 89.2005 |
| | 0.032 ng/ml | 19.25 | 19.75 | 19.42 | 19.48 | 78.6211 |
| | 0.0064 ng/ml | 17.99 | 19.32 | 19.60 | 18.97 | 65.0898 |
| Treatment group | 100 ng/ml | 19.55 | 18.92 | 19.07 | 19.18 | 74.0025 |
| | 20 ng/ml | 19.45 | 19.24 | 18.56 | 19.08 | 71.7160 |
| | 4 ng/ml | 19.57 | 18.94 | 18.35 | 18.95 | 68.4938 |
| | 0.8 ng/ml | 22.14 | 19.38 | 19.38 | 20.30 | 84.4259 |
| | 0.16 ng/ml | 18.67 | 18.46 | 18.08 | 18.40 | 55.4565 |
| | 0.032 ng/ml | 18.77 | 18.29 | 17.90 | 18.32 | 52.3506 |
| | 0.0064 ng/ml | 18.15 | 18.24 | 17.40 | 17.93 | 36.8071 |
| Positive control group (Remdesivir) | 10 μM | 34.85 | 33.56 | 34.75 | 34.39 | 99.9994 |
| | 3 μM | 30.57 | 33.96 | 33.11 | 32.55 | 99.9980 |
| | 1 μM | 27.63 | 26.97 | 26.91 | 27.17 | 99.9173 |
| | 0.3 μM | 20.83 | 20.76 | 19.75 | 20.45 | 91.2627 |
| | 0.1 μM | 17.63 | 17.75 | 17.57 | 17.65 | 39.2903 |
| | 0.03 μM | 17.05 | 16.86 | 17.71 | 17.21 | 17.4504 |
| Negative control group | 0 | 17.34 | 17.18 | 17.15 | 17.23 | 0 |

It can be seen from the above results that, the test drug at the concentrations of 0.0064 ng/ml and above in the prevention group has an inhibitory effect on the replication and infection of novel coronavirus, wherein the inhibition rate of the test drug at the concentrations of 4 ng/ml and above reaches 98% or more; the test drug at the concentrations of 0.0064 ng/ml and above in the treatment group has an certain inhibitory effect on the replication and infection of novel coronavirus, but the inhibitory effect is poorer than that of the prevention group, and except for 0.8 ng/mL, each of them is less than 75%. In the positive control group, Remdesivir at concentrations of 0.3 UM and above has 90% or more inhibition against the virus.

It is calculated that, for the test drug, in the prevention group, $IC_{50}$=0.0196 ng/mL; in the treatment group, $IC_{50}$=0.0612 ng/mL, in the positive control group, $IC_{50}$=0.12 μmol/L. It is calculated that, for the test drug, in the prevention group, the safety index SI >106, in the treatment group, the safety index SI was >$3.2\times10^5$; showing good cytotoxic selectivity.

2.2.2 Immunofluorescence Assay

The supernatant of the cell culture in the above 48-well plate was sucked out, and the cells were washed with PBS; 200 μL of iced 80% acetone solution was added to each well to fix at 4° C. for 30 min; after the cells were washed with PBS, 200 μL PBS containing 3% BSA was added to block at room temperature for 30 min; and after PBS washing, 200 μl of primary antibody (rabbit anti-SARS-COV2 NP, diluted 2000 times) protein serum (Beijing Sino Biological Co., Ltd.) was added to incubate overnight at 4° C. After the primary antibody was sucked out, the cells were washed with PBS, then adding 200 μL of FITC-labeled rabbit anti-rabbit IgG secondary antibody (Jackson) (diluted 1500 times), and incubating at room temperature for 2 h. After the secondary antibody was sucked out, the cells were washed with PBS, then adding 200 μL of DAPI (diluted with PBS in a ratio of 1:500), and incubating for 5 min at room temperature in the dark. After the DAPI staining solution was sucked out, the cells were washed with PBS, and microscopic examination was performed.

Figure 21:
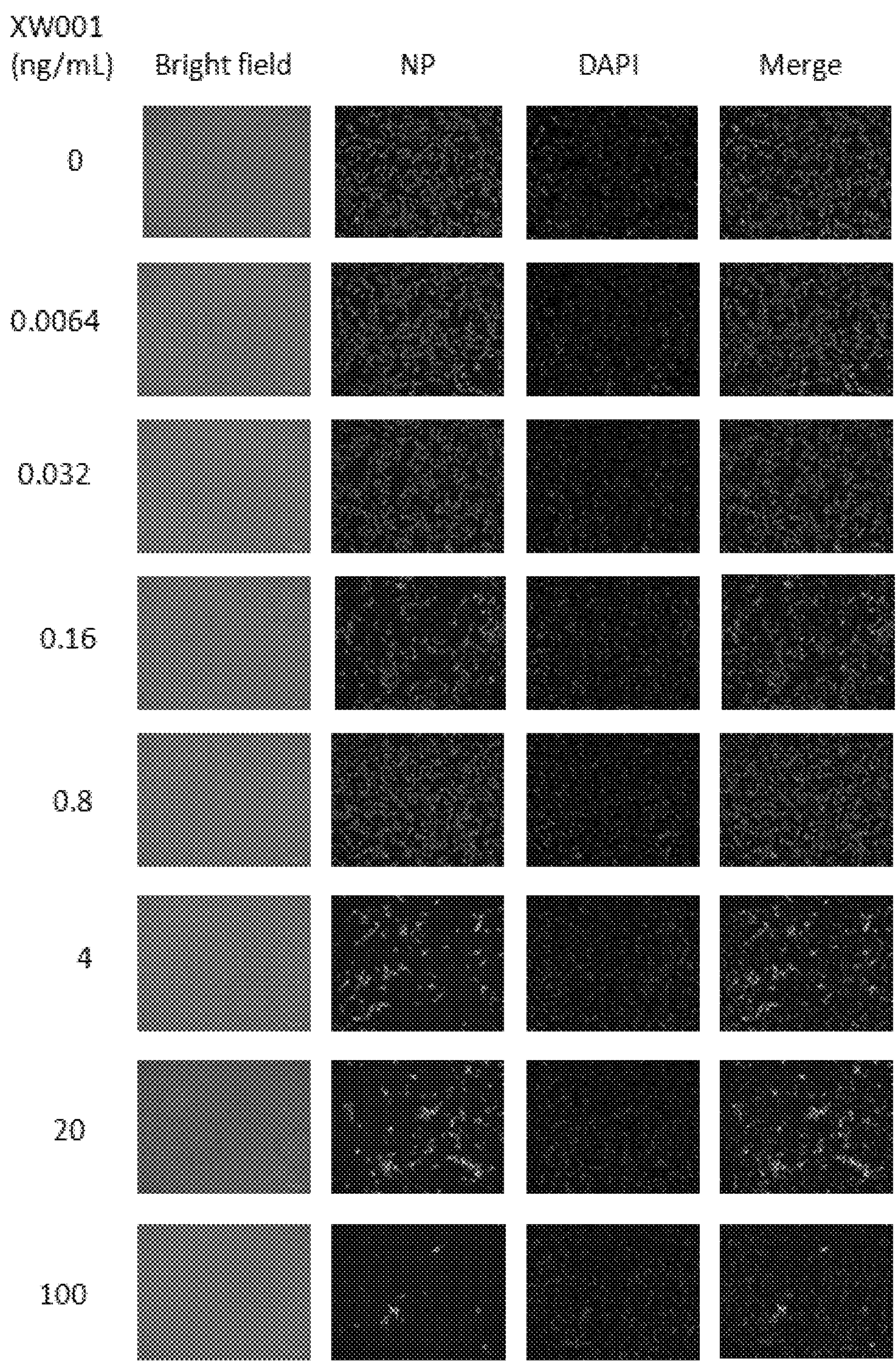
FIG. 21 shows the inhibitory effect of different concentrations of the tested drugs on Vero cells infected with the novel coronavirus in the prevention group.
Figure 22:
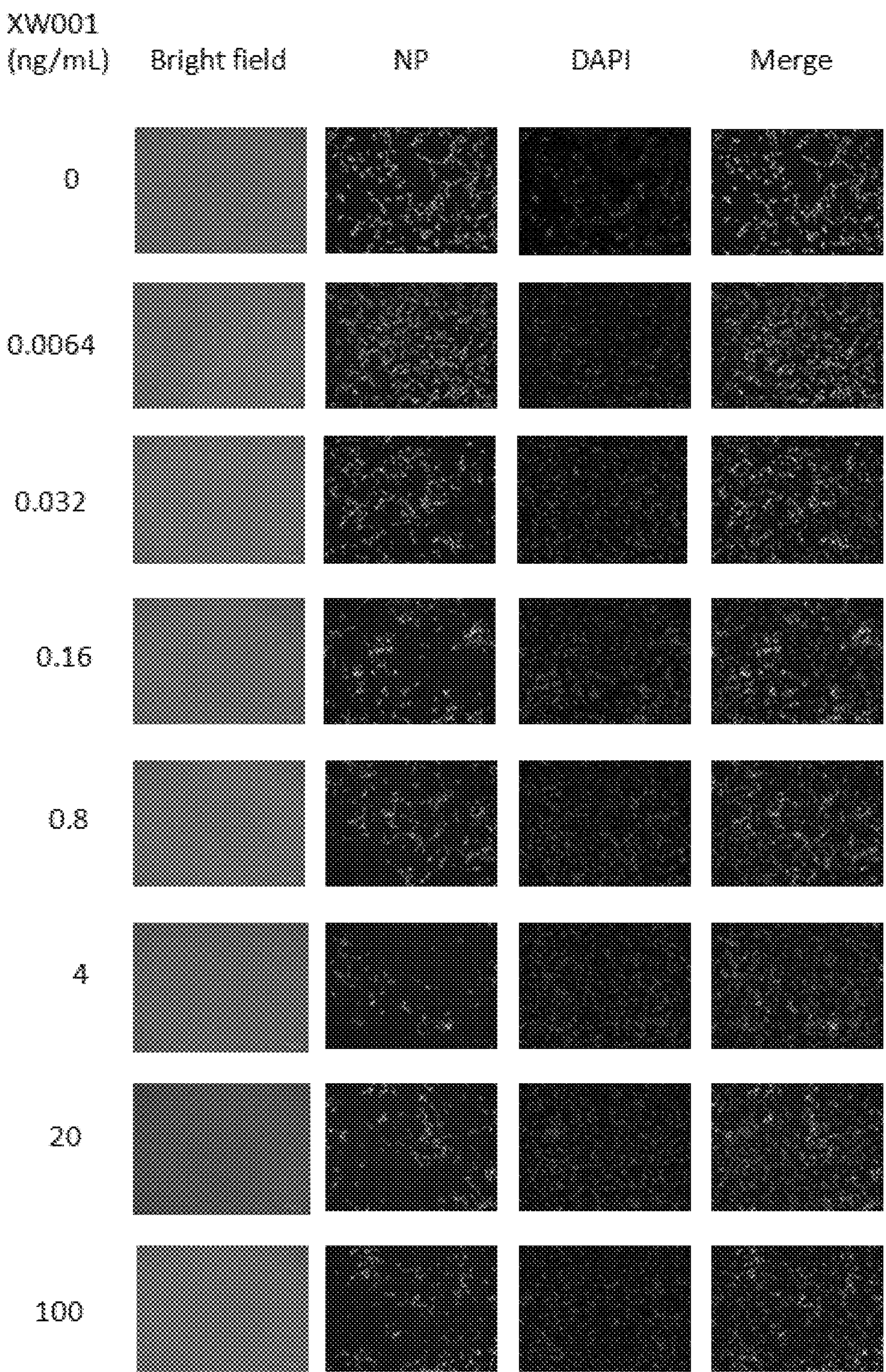
FIG. 22 shows the inhibitory effect of different concentrations of the tested drugs on Vero cells infected with novel coronavirus in the treatment group.
Figure 23:
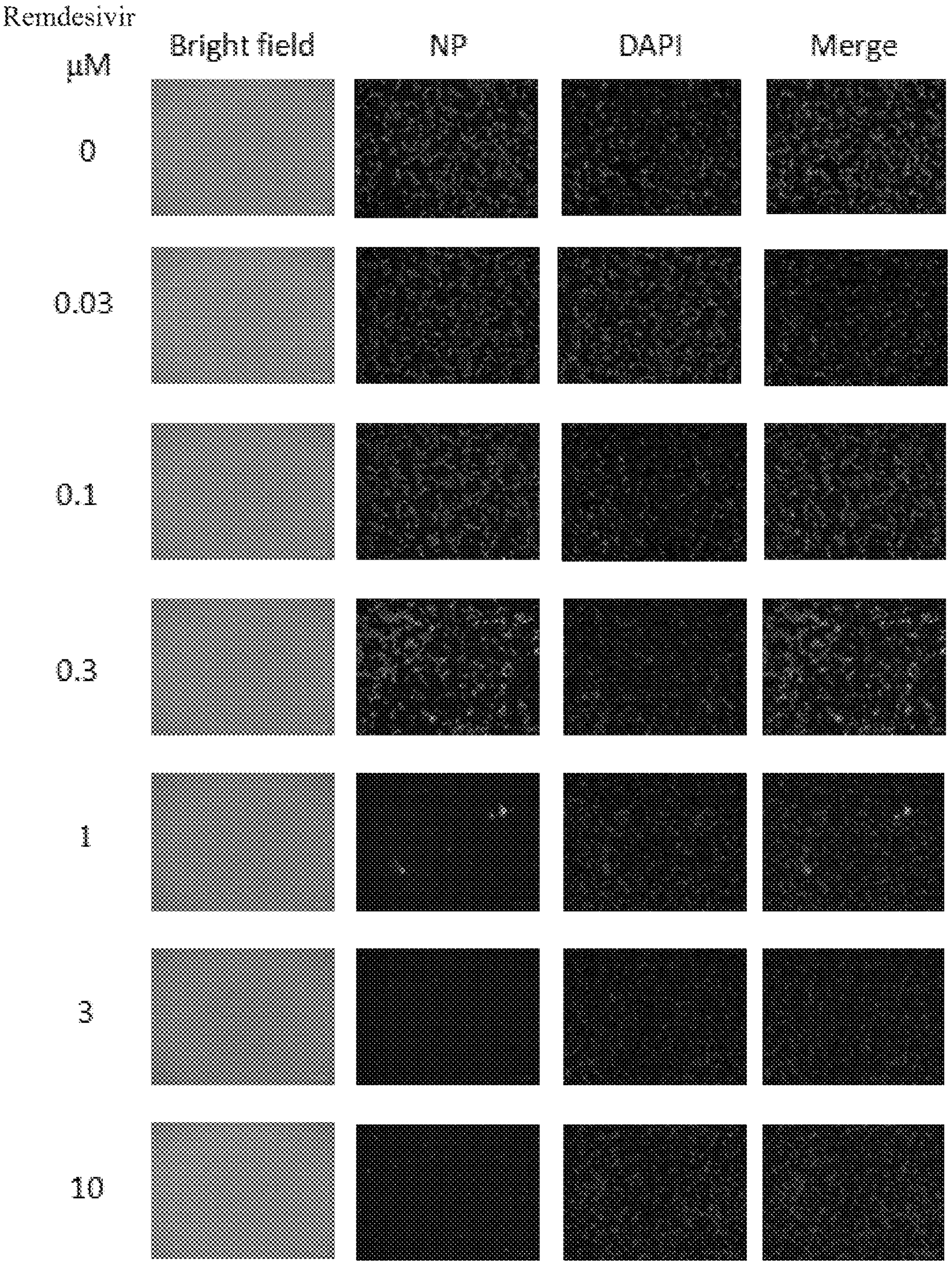
FIG. 23 shows the inhibitory effect of different concentrations of Remdesivir on Vero cells infected with novel coronavirus.

The immunofluorescence results are consistent with those in the nucleic acid assay, the test drug at the concentrations of 0.032 ng/ml and above in the prevention group has a certain inhibitory effect on the in vitro infection of the novel coronavirus, wherein the test drugs at concentrations of 4 ng/mL and above has a significant inhibitory effect on the viral infection; the test drug at the concentrations of 0.032 ng/mL and above in the treatment group has certain inhibitory effect on the in vitro infection of novel coronavirus, but the inhibitory effect is lower than that in the prevention group. Remdesivir at the concentrations of 0.3 μM and above in the positive control group has a significant inhibitory effect on viral infection in vitro. The specific results are shown in FIG. 21, FIG. 22 and FIG. 23.

SEQUENCE LISTING:

SEQ ID NO: 1

KPTTTGKGCHIGRFKSLSPQELASFKKARDALEESLKLKNWSCSSPVFP

GNWDLRLLQVRERPVALEAELALTLKVLEAAAGPALEDVLDQPLHTLHH

-continued

ILSQLQACIQPQPTAGPRPRGRLHHWLHRLQEAPKKESAGCLEASVTFN

LFRLLTRDLKYVADGNLCLRTSTHPEST

SEQ ID NO: 2

GPVPTSKPTTTGKGCHIGRFKSLSPQELASFKKARDALEESLKLKNWSC

SSPVFPGNWDLRLLQVRERPVALEAELALTLKVLEAAAGPALEDVLDQP

LHTLHHILSQLQACIQPQPTAGPRPRGRLHHWLHRLQEAPKKESAGCLE

ASVTFNLFRLLTRDLKYVADGNLCLRTSTHPEST

SEQ ID NO: 3

MAAAWTVVLVTLVLGLAVAGPVPTSKPTTTGKGCHIGRFKSLSPQELAS

FKKARDALEESLKLKNWSCSSPVFPGNWDLRLLQVRERPVALEAELALT

LKVLEAAAGPALEDVLDQPLHTLHHILSQLQACIQPQPTAGPRPRGRLH

HWLHRLQEAPKKESAGCLEASVTFNLFRLLTRDLKYVADGNLCLRTSTH

PEST

SEQ ID NO: 4

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVAEGNLCLRTSTHPEST

SEQ ID NO: 5

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVAEGNLSLRTSTHPEST

SEQ ID NO: 6

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVASGNLCLRTSTHPEST

SEQ ID NO: 7

MKPTTTGKGCHIGRFKSLSPQELASFKKARDALEESLKLKNWSCSSPVF

PGNWDLRLLQVRERPVALEAELALILKVLEAAAGPALEDVLDQPLHTLH

HILSQLQACIQPQPTAGPRPRGRLHHWLHRLQEAPKKESAGCLEASVTF

NLFRLLTRDLKYVASGNLSLRTSTHPEST

SEQ ID NO: 8

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVADANLCLRTSTHPEST

SEQ ID NO: 9

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVADANLSLRTSTHPEST

-continued

SEQ ID NO: 10

MKPTTTGKGCHIGRFKSLSPQELASFKKARDALEESLKLKNWSCSSPVF

PGNWDLRLLQVRERPVALEAELALTLKVLEAAAGPALEDVLDQPLHTLH

HILSQLQACIQPQPTAGPRPRGRLHHWLHRLQEAPKKESAGCLEASVTF

NLFRLLTRDLKYVADGNLSLRTSTHPEST

SEQ ID NO: 11

ATGAAACCGACCACGACCGGCAAAGGCTGCCATATTGGTCGCTTTAAGT

CGCTGTCGCCGCAGGAACTGGCGAGCTTCAAGAAAGCCCGTGATGCCCT

GGAGGAATCGCTGAAACTGAAGAACTGGAGCTGTAGCTCGCCGGTGTTC

CCGGGCAACTGGGATCTGCGTCTGCTGCAGGTTCGCGAACGTCCGGTTG

CGCTGGAAGCGGAACTGGCGCTGACCCTGAAAGTGCTGGAAGCGGCAGC

GGGTCCGGCGCTGGAAGATGTTCTGGATCAGCCGCTGCACACCCTGCAT

CATATTCTGTCGCAGCTGCAGGCGTGCATTCAACCGCAGCCGACCGCGG

GCCCGCGTCCGCGCGGC3CGTCTGCATCACTGGCTGCACCGTCTGCAGG

AAGCCCCGAAGAAAGAGTCGGCGGGCTGTCTGGAAGCGTCGGTGACCTT

CAATCTGTTCCGTCTGCTGACCCGTGATCTGAAATACGTTGCGGAAGGC

AATCTGTCTCTGCGTACCTCGACCCACCCGGAATCGACC

SEQ ID NO: 12

ATGAAACCGACCACGACCGGCAAAGGCTGCCATATTGGTCGCTTTAAGT

CGCTGTCGCCGCAGGAACTGGCGAGCTTCAAGAAAGCCCGTGATGCCCT

GGAGGAATCGCTGAAACTGAAGAACTGGAGCTGTAGCTCGCCGGTGTTC

CCGGGCAACTGGGATCTGCGTCTGCTGCAGGTTCGCGAACGTCCGGTTG

CGCTGGAAGCGGAACTGGCGCTGACCCTGAAAGTGCTGGAAGCGGCAGC

GGGTCCGGCGCTGGAAGATGTTCTGGATCAGCCGCTGCACACCCTGCAT

CATATTCTGTCGCAGCTGCAGGCGTGCATTCAACCGCAGCCGACCGCGG

GCCCGCGTCCGCGCGGC3CGTCTGCATCACTGGCTGCACCGTCTGCAGG

AAGCCCCGAAGAAAGAGTCGGCGGGCTGTCTGGAAGCGTCGGTGACCTT

CAATCTGTTCCGTCTGCTGACCCGTGATCTGAAATACGTTGCGAGCGGC

AATCTGTCTCTGCGTACCTCGACCCACCCGGAATCGACCTAATAATAA

SEQ ID NO: 13

ATGAAACCGACCACGACCGGCAAAGGCTGCCATATTGGTCGCTTTAAGT

CGCTGTCGCCGCAGGAACTGGCGAGCTTCAAGAAAGCCCGTGATGCCCT

GGAGGAATCGCTGAAACTGAAGAACTGGAGCTGTAGCTCGCCGGTGTTC

CCGGGCAACTGGGATCTGCGTCTGCTGCAGGTTCGCGAACGTCCGGTTG

CGCTGGAAGCGGAACTGGCGCTGACCCTGAAAGTGCTGGAAGCGGCAGC

GGGTCCGGCGCTGGAAGATGTTCTGGATCAGCCGCTGCACACCCTGCAT

CATATTCTGTCGCAGCTGCAGGCGTGCATTCAACCGCAGCCGACCGCGG

GCCCGCGTCCGCGCGGC3CGTCTGCATCACTGGCTGCACCGTCTGCAGG

AAGCCCCGAAGAAAGAGTCGGCGGGCTGTCTGGAAGCGTCGGTGACCTT

CAATCTGTTCCGTCTGCTGACCCGTGATCTGAAATACGTTGCGGACGCG

AATCTGTCTCTGCGTACCTCGACCCACCCGGAATCGACCTAATAATAA

-continued

SEQ ID NO: 14

ATGAAACCGACCACGACCGGCAAAGGCTGCCATATTGGTCGCTTTAAGT
CGCTGTCGCCGCAGGAACTGGCGAGCTTCAAGAAAGCCCGTGATGCCCT
GGAGGAATCGCTGAAACTGAAGAACTGGAGCTGTAGCTCGCCGGTGTTC
CCGGGCAACTGGGATCTGCGTCTGCTGCAGGTTCGCGAACGTCCGGTTG
CGCTGGAAGCGGAACTGGCGCTGACCCTGAAAGTGCTGGAAGCGGCAGC
GGGTCCGGCGCTGGAAGATGTTCTGGATCAGCCGCTGCACACCCTGCAT
CATATTCTGTCGCAGCTGCAGGCGTGCATTCAACCGCAGCCGACCGCGG
GCCCGCGTCCGCGCGGC3CGTCTGCATCACTGGCTGCACCGTCTGCAGG
AAGCCCCGAAGAAAGAGTCGGCGGGCTGTCTGGAAGCGTCGGTGACCTT
CAATCTGTTCCGTCTGCTGACCCGTGATCTGAAATACGTTGCGGAAGGC
AATCTGTGTCTGCGTACCTCGACCCACCCGGAATCGACC

SEQ ID NO: 15

ATGAAACCGACCACGACCGGCAAAGGCTGCCATATTGGTCGCTTTAAGT
CGCTGTCGCCGCAGGAACTGGCGAGCTTCAAGAAAGCCCGTGATGCCCT
GGAGGAATCGCTGAAACTGAAGAACTGGAGCTGTAGCTCGCCGGTGTTC
CCGGGCAACTGGGATCTGCGTCTGCTGCAGGTTCGCGAACGTCCGGTTG
CGCTGGAAGCGGAACTGGCGCTGACCCTGAAAGTGCTGGAAGCGGCAGC
GGGTCCGGCGCTGGAAGATGTTCTGGATCAGCCGCTGCACACCCTGCAT
CATATTCTGTCGCAGCTGCAGGCGTGCATTCAACCGCAGCCGACCGCGG
GCCCGCGTCCGCGCGGC3CGTCTGCATCACTGGCTGCACCGTCTGCAGG
AAGCCCCGAAGAAAGAGTCGGCGGGCTGTCTGGAAGCGTCGGTGACCTT
CAATCTGTTCCGTCTGCTGACCCGTGATCTGAAATACGTTGCGAGCGGC
AATCTGTGTCTGCGTACCTCGACCCACCCGGAATCGACCTAATAATAA

SEQ ID NO: 16

ATGAAACCGACCACGACCGGCAAAGGCTGCCATATTGGTCGCTTTAAGT
CGCTGTCGCCGCAGGAACTGGCGAGCTTCAAGAAAGCCCGTGATGCCCT
GGAGGAATCGCTGAAACTGAAGAACTGGAGCTGTAGCTCGCCGGTGTTC
CCGGGCAACTGGGATCTGCGTCTGCTGCAGGTTCGCGAACGTCCGGTTG
CGCTGGAAGCGGAACTGGCGCTGACCCTGAAAGTGCTGGAAGCGGCAGC
GGGTCCGGCGCTGGAAGATGTTCTGGATCAGCCGCTGCACACCCTGCAT
CATATTCTGTCGCAGCTGCAGGCGTGCATTCAACCGCAGCCGACCGCGG
GCCCGCGTCCGCGCGGC3CGTCTGCATCACTGGCTGCACCGTCTGCAGG
AAGCCCCGAAGAAAGAGTCGGCGGGCTGTCTGGAAGCGTCGGTGACCTT
CAATCTGTTCCGTCTGCTGACCCGTGATCTGAAATACGTTGCGGACGCG
AATCTGTGTCTGCGTACCTCGACCCACCCGGAATCGACCTAATAATAA

SEQ ID NO: 17

ATGAAACCGACCACGACCGGCAAAGGCTGCCATATTGGTCGCTTTAAGT
CGCTGTCGCCGCAGGAACTGGCGAGCTTCAAGAAAGCCCGTGATGCCCT
GGAGGAATCGCTGAAACTGAAGAACTGGAGCTGTAGCTCGCCGGTGTTC
CCGGGCAACTGGGATCTGCGTCTGCTGCAGGTTCGCGAACGTCCGGTTG
CGCTGGAAGCGGAACTGGCGCTGACCCTGAAAGTGCTGGAAGCGGCAGC
GGGTCCGGCGCTGGAAGATGTTCTGGATCAGCCGCTGCACACCCTGCAT
CATATTCTGTCGCAGCTGCAGGCGTGCATTCAACCGCAGCCGACCGCGG
GCCCGCGTCCGCGCGGC3CGTCTGCATCACTGGCTGCACCGTCTGCAGG
AAGCCCCGAAGAAAGAGTCGGCGGGCTGTCTGGAAGCGTCGGTGACCTT
CAATCTGTTCCGTCTGCTGACCCGTGATCTGAAATACGTTGCGGACGGC
AATCTGTCTCTGCGTACCTCGACCCACCCGGAATCGACCTAATAATAA

SEQ ID NO: 18

AAACCGACCACGACCGGCAAAGGCTGCCATATTGGTCGCTTTAAGTCGC
TGTCGCCGCAGGAACTGGCGAGCTTCAAGAAAGCCCGTGATGCCCTGGA
GGAATCGCTGAAACTGAAGAACTGGAGCTGTAGCTCGCCGGTGTTCCCG
GGCAACTGGGATCTGCGTCTGCTGCAGGTTCGCGAACGTCCGGTTGCGC
TGGAAGCGGAACTGGCGCTGACCCTGAAAGTGCTGGAAGCGGCAGCGGG
TCCGGCGCTGGAAGATGTTCTGGATCAGCCGCTGCACACCCTGCATCAT
ATTCTGTCGCAGCTGCAGGCGTGCATTCAACCGCAGCCGACCGCGGGCC
CGCGTCCGCGCGGCCGT3CTGCATCACTGGCTGCACCGTCTGCAGGAAG
CCCCGAAGAAAGAGTCGGCGGGCTGTCTGGAAGCGTCGGTGACCTTCAA
TCTGTTCCGTCTGCTGACCCGTGATCTGAAATACGTTGCGGACGGCAAT
CTGTGTCTGCGTACCTCGACCCACCCGGAATCGACCTAATAATAA

The invention claimed is:

1. A method for treating a viral infectious disease or a tumor, comprising administering to a subject an effective amount of an interleukin 29 (IL-29) mutant protein, wherein the protein consists of the amino acid sequence of SEQ ID NO: 5 or SEQ ID NO: 9.

2. The method according to claim 1, wherein the viral infectious disease is a respiratory disease or hepatitis caused by viral infection.

3. The method according to claim 1, wherein the protein is used in combination with one or more other medicaments.

4. The method according to claim 3, wherein the one or more medicaments comprises an antiviral agent, a chemotherapeutic agent, an immunomodulatory agent, and an anti-inflammatory agent.

5. The method according to claim 1, wherein the viral infectious disease is caused by infection of SARS-COV-2.

6. A method for treating a viral infectious disease or a tumor, comprising administering to a subject an effective amount of a pharmaceutical composition comprising an interleukin 29 (IL-29) mutant protein, wherein the protein consists of SEQ ID NO: 5 or SEQ ID NO: 9.

* * * * *

SEQUENCE LISTING

<160> NUMBER OF SEQ ID NOS: 18

<210> SEQ ID NO 1
<211> LENGTH: 175
<212> TYPE: PRT
<213> ORGANISM: Artificial Sequence
<220> FEATURE:
<223> OTHER INFORMATION: Synthetic

<400> SEQUENCE: 1

```
Lys Pro Thr Thr Thr Gly Lys Gly Cys His Ile Gly Arg Phe Lys Ser
1               5                   10                  15

Leu Ser Pro Gln Glu Leu Ala Ser Phe Lys Lys Ala Arg Asp Ala Leu
            20                  25                  30
```

```
Glu Glu Ser Leu Lys Leu Lys Asn Trp Ser Cys Ser Ser Pro Val Phe
        35                  40                  45

Pro Gly Asn Trp Asp Leu Arg Leu Leu Gln Val Arg Glu Arg Pro Val
    50                  55                  60

Ala Leu Glu Ala Glu Leu Ala Leu Thr Leu Lys Val Leu Glu Ala Ala
65                  70                  75                  80

Ala Gly Pro Ala Leu Glu Asp Val Leu Asp Gln Pro Leu His Thr Leu
                85                  90                  95

His His Ile Leu Ser Gln Leu Gln Ala Cys Ile Gln Pro Gln Pro Thr
            100                 105                 110

Ala Gly Pro Arg Pro Arg Gly Arg Leu His His Trp Leu His Arg Leu
        115                 120                 125

Gln Glu Ala Pro Lys Lys Glu Ser Ala Gly Cys Leu Glu Ala Ser Val
    130                 135                 140

Thr Phe Asn Leu Phe Arg Leu Leu Thr Arg Asp Leu Lys Tyr Val Ala
145                 150                 155                 160

Asp Gly Asn Leu Cys Leu Arg Thr Ser Thr His Pro Glu Ser Thr
                165                 170                 175


<210> SEQ ID NO 2
<211> LENGTH: 181
<212> TYPE: PRT
<213> ORGANISM: Artificial Sequence
<220> FEATURE:
<223> OTHER INFORMATION: Synthetic

<400> SEQUENCE: 2

Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Cys Leu Arg Thr Ser Thr
                165                 170                 175

His Pro Glu Ser Thr
            180


<210> SEQ ID NO 3
<211> LENGTH: 200
<212> TYPE: PRT
<213> ORGANISM: Artificial Sequence
<220> FEATURE:
```

```
<223> OTHER INFORMATION: Synthetic

<400> SEQUENCE: 3

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200


<210> SEQ ID NO 4
<211> LENGTH: 176
<212> TYPE: PRT
<213> ORGANISM: Artificial Sequence
<220> FEATURE:
<223> OTHER INFORMATION: Synthetic

<400> SEQUENCE: 4

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140
```

```
Val Thr Phe Asn Leu Phe Arg Leu Leu Thr Arg Asp Leu Lys Tyr Val
145                 150                 155                 160

Ala Glu Gly Asn Leu Cys Leu Arg Thr Ser Thr His Pro Glu Ser Thr
                165                 170                 175


<210> SEQ ID NO 5
<211> LENGTH: 176
<212> TYPE: PRT
<213> ORGANISM: Artificial Sequence
<220> FEATURE:
<223> OTHER INFORMATION: Synthetic

<400> SEQUENCE: 5

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Glu Gly Asn Leu Ser Leu Arg Thr Ser Thr His Pro Glu Ser Thr
                165                 170                 175


<210> SEQ ID NO 6
<211> LENGTH: 176
<212> TYPE: PRT
<213> ORGANISM: Artificial Sequence
<220> FEATURE:
<223> OTHER INFORMATION: Synthetic

<400> SEQUENCE: 6

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
```

```
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Ser Gly Asn Leu Cys Leu Arg Thr Ser Thr His Pro Glu Ser Thr
                165                 170                 175


<210> SEQ ID NO 7
<211> LENGTH: 176
<212> TYPE: PRT
<213> ORGANISM: Artificial Sequence
<220> FEATURE:
<223> OTHER INFORMATION: Synthetic

<400> SEQUENCE: 7

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Ser Gly Asn Leu Ser Leu Arg Thr Ser Thr His Pro Glu Ser Thr
                165                 170                 175


<210> SEQ ID NO 8
<211> LENGTH: 176
<212> TYPE: PRT
<213> ORGANISM: Artificial Sequence
<220> FEATURE:
<223> OTHER INFORMATION: Synthetic

<400> SEQUENCE: 8

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60
```

```
Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Ala Asn Leu Cys Leu Arg Thr Ser Thr His Pro Glu Ser Thr
                165                 170                 175


<210> SEQ ID NO 9
<211> LENGTH: 176
<212> TYPE: PRT
<213> ORGANISM: Artificial Sequence
<220> FEATURE:
<223> OTHER INFORMATION: Synthetic

<400> SEQUENCE: 9

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Ala Asn Leu Ser Leu Arg Thr Ser Thr His Pro Glu Ser Thr
                165                 170                 175


<210> SEQ ID NO 10
<211> LENGTH: 176
<212> TYPE: PRT
<213> ORGANISM: Artificial Sequence
<220> FEATURE:
<223> OTHER INFORMATION: Synthetic

<400> SEQUENCE: 10

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30
```

```
Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Gly Asn Leu Ser Leu Arg Thr Ser Thr His Pro Glu Ser Thr
                165                 170                 175
```

<210> SEQ ID NO 11
<211> LENGTH: 528
<212> TYPE: DNA
<213> ORGANISM: Artificial Sequence
<220> FEATURE:
<223> OTHER INFORMATION: Synthetic

<400> SEQUENCE: 11

```
atgaaaccga ccacgaccgg caaaggctgc catattggtc gctttaagtc gctgtcgccg     60

caggaactgg cgagcttcaa gaaagcccgt gatgccctgg aggaatcgct gaaactgaag    120

aactggagct gtagctcgcc ggtgttcccg ggcaactggg atctgcgtct gctgcaggtt    180

cgcgaacgtc cggttgcgct ggaagcggaa ctggcgctga ccctgaaagt gctggaagcg    240

gcagcgggtc cggcgctgga agatgttctg gatcagccgc tgcacaccct gcatcatatt    300

ctgtcgcagc tgcaggcgtg cattcaaccg cagccgaccg cgggcccgcg tccgcgcggc    360

cgtctgcatc actggctgca ccgtctgcag gaagccccga agaaagagtc ggcgggctgt    420

ctggaagcgt cggtgacctt caatctgttc cgtctgctga cccgtgatct gaaatacgtt    480

gcggaaggca atctgtctct gcgtacctcg acccacccgg aatcgacc                528
```

<210> SEQ ID NO 12
<211> LENGTH: 537
<212> TYPE: DNA
<213> ORGANISM: Artificial Sequence
<220> FEATURE:
<223> OTHER INFORMATION: Synthetic

<400> SEQUENCE: 12

```
atgaaaccga ccacgaccgg caaaggctgc catattggtc gctttaagtc gctgtcgccg     60

caggaactgg cgagcttcaa gaaagcccgt gatgccctgg aggaatcgct gaaactgaag    120

aactggagct gtagctcgcc ggtgttcccg ggcaactggg atctgcgtct gctgcaggtt    180

cgcgaacgtc cggttgcgct ggaagcggaa ctggcgctga ccctgaaagt gctggaagcg    240

gcagcgggtc cggcgctgga agatgttctg gatcagccgc tgcacaccct gcatcatatt    300

ctgtcgcagc tgcaggcgtg cattcaaccg cagccgaccg cgggcccgcg tccgcgcggc    360

cgtctgcatc actggctgca ccgtctgcag gaagccccga agaaagagtc ggcgggctgt    420
```

ctggaagcgt cggtgacctt caatctgttc cgtctgctga cccgtgatct gaaatacgtt 480
gcgagcggca atctgtctct gcgtacctcg acccacccgg aatcgaccta ataataa 537

<210> SEQ ID NO 13
<211> LENGTH: 537
<212> TYPE: DNA
<213> ORGANISM: Artificial Sequence
<220> FEATURE:
<223> OTHER INFORMATION: Synthetic

<400> SEQUENCE: 13
atgaaaccga ccacgaccgg caaaggctgc catattggtc gctttaagtc gctgtcgccg 60
caggaactgg cgagcttcaa gaaagcccgt gatgccctgg aggaatcgct gaaactgaag 120
aactggagct gtagctcgcc ggtgttcccg ggcaactggg atctgcgtct gctgcaggtt 180
cgcgaacgtc cggttgcgct ggaagcggaa ctggcgctga ccctgaaagt gctggaagcg 240
gcagcgggtc cggcgctgga agatgttctg gatcagccgc tgcacaccct gcatcatatt 300
ctgtcgcagc tgcaggcgtg cattcaaccg cagccgaccg cgggcccgcg tccgcgcggc 360
cgtctgcatc actggctgca ccgtctgcag gaagccccga agaaagagtc ggcgggctgt 420
ctggaagcgt cggtgacctt caatctgttc cgtctgctga cccgtgatct gaaatacgtt 480
gcggacgcga atctgtctct gcgtacctcg acccacccgg aatcgaccta ataataa 537

<210> SEQ ID NO 14
<211> LENGTH: 528
<212> TYPE: DNA
<213> ORGANISM: Artificial Sequence
<220> FEATURE:
<223> OTHER INFORMATION: Synthetic

<400> SEQUENCE: 14
atgaaaccga ccacgaccgg caaaggctgc catattggtc gctttaagtc gctgtcgccg 60
caggaactgg cgagcttcaa gaaagcccgt gatgccctgg aggaatcgct gaaactgaag 120
aactggagct gtagctcgcc ggtgttcccg ggcaactggg atctgcgtct gctgcaggtt 180
cgcgaacgtc cggttgcgct ggaagcggaa ctggcgctga ccctgaaagt gctggaagcg 240
gcagcgggtc cggcgctgga agatgttctg gatcagccgc tgcacaccct gcatcatatt 300
ctgtcgcagc tgcaggcgtg cattcaaccg cagccgaccg cgggcccgcg tccgcgcggc 360
cgtctgcatc actggctgca ccgtctgcag gaagccccga agaaagagtc ggcgggctgt 420
ctggaagcgt cggtgacctt caatctgttc cgtctgctga cccgtgatct gaaatacgtt 480
gcggaaggca atctgtgtct gcgtacctcg acccacccgg aatcgacc 528

<210> SEQ ID NO 15
<211> LENGTH: 537
<212> TYPE: DNA
<213> ORGANISM: Artificial Sequence
<220> FEATURE:
<223> OTHER INFORMATION: Synthetic

<400> SEQUENCE: 15
atgaaaccga ccacgaccgg caaaggctgc catattggtc gctttaagtc gctgtcgccg 60
caggaactgg cgagcttcaa gaaagcccgt gatgccctgg aggaatcgct gaaactgaag 120
aactggagct gtagctcgcc ggtgttcccg ggcaactggg atctgcgtct gctgcaggtt 180
cgcgaacgtc cggttgcgct ggaagcggaa ctggcgctga ccctgaaagt gctggaagcg 240

```
gcagcgggtc cggcgctgga agatgttctg gatcagccgc tgcacaccct gcatcatatt    300

ctgtcgcagc tgcaggcgtg cattcaaccg cagccgaccg cgggcccgcg tccgcgcggc    360

cgtctgcatc actggctgca ccgtctgcag gaagccccga agaaagagtc ggcgggctgt    420

ctggaagcgt cggtgacctt caatctgttc cgtctgctga cccgtgatct gaaatacgtt    480

gcgagcggca atctgtgtct gcgtacctcg acccacccgg aatcgaccta ataataa       537
```

```
<210> SEQ ID NO 16
<211> LENGTH: 537
<212> TYPE: DNA
<213> ORGANISM: Artificial Sequence
<220> FEATURE:
<223> OTHER INFORMATION: Synthetic

<400> SEQUENCE: 16

atgaaaccga ccacgaccgg caaaggctgc catattggtc gctttaagtc gctgtcgccg     60

caggaactgg cgagcttcaa gaaagcccgt gatgccctgg aggaatcgct gaaactgaag    120

aactggagct gtagctcgcc ggtgttcccg ggcaactggg atctgcgtct gctgcaggtt    180

cgcgaacgtc cggttgcgct ggaagcggaa ctggcgctga ccctgaaagt gctggaagcg    240

gcagcgggtc cggcgctgga agatgttctg gatcagccgc tgcacaccct gcatcatatt    300

ctgtcgcagc tgcaggcgtg cattcaaccg cagccgaccg cgggcccgcg tccgcgcggc    360

cgtctgcatc actggctgca ccgtctgcag gaagccccga agaaagagtc ggcgggctgt    420

ctggaagcgt cggtgacctt caatctgttc cgtctgctga cccgtgatct gaaatacgtt    480

gcggacgcga atctgtgtct gcgtacctcg acccacccgg aatcgaccta ataataa       537
```

```
<210> SEQ ID NO 17
<211> LENGTH: 537
<212> TYPE: DNA
<213> ORGANISM: Artificial Sequence
<220> FEATURE:
<223> OTHER INFORMATION: Synthetic

<400> SEQUENCE: 17

atgaaaccga ccacgaccgg caaaggctgc catattggtc gctttaagtc gctgtcgccg     60

caggaactgg cgagcttcaa gaaagcccgt gatgccctgg aggaatcgct gaaactgaag    120

aactggagct gtagctcgcc ggtgttcccg ggcaactggg atctgcgtct gctgcaggtt    180

cgcgaacgtc cggttgcgct ggaagcggaa ctggcgctga ccctgaaagt gctggaagcg    240

gcagcgggtc cggcgctgga agatgttctg gatcagccgc tgcacaccct gcatcatatt    300

ctgtcgcagc tgcaggcgtg cattcaaccg cagccgaccg cgggcccgcg tccgcgcggc    360

cgtctgcatc actggctgca ccgtctgcag gaagccccga agaaagagtc ggcgggctgt    420

ctggaagcgt cggtgacctt caatctgttc cgtctgctga cccgtgatct gaaatacgtt    480

gcggacggca atctgtctct gcgtacctcg acccacccgg aatcgaccta ataataa       537
```

```
<210> SEQ ID NO 18
<211> LENGTH: 534
<212> TYPE: DNA
<213> ORGANISM: Artificial Sequence
<220> FEATURE:
<223> OTHER INFORMATION: Synthetic

<400> SEQUENCE: 18

aaaccgacca cgaccggcaa aggctgccat attggtcgct ttaagtcgct gtcgccgcag     60

gaactggcga gcttcaagaa agcccgtgat gccctggagg aatcgctgaa actgaagaac    120
```

-continued

```
tggagctgta gctcgccggt gttcccgggc aactgggatc tgcgtctgct gcaggttcgc    180

gaacgtccgg ttgcgctgga agcggaactg gcgctgaccc tgaaagtgct ggaagcggca    240

gcgggtccgg cgctggaaga tgttctggat cagccgctgc acaccctgca tcatattctg    300

tcgcagctgc aggcgtgcat tcaaccgcag ccgaccgcgg gcccgcgtcc gcgcggccgt    360

ctgcatcact ggctgcaccg tctgcaggaa gccccgaaga aagagtcggc gggctgtctg    420

gaagcgtcgg tgaccttcaa tctgttccgt ctgctgaccc gtgatctgaa atacgttgcg    480

gacggcaatc tgtgtctgcg tacctcgacc cacccggaat cgacctaata ataa          534
```